(12) United States Patent
Cho et al.

(10) Patent No.: US 11,969,397 B2
(45) Date of Patent: Apr. 30, 2024

(54) COMPOSITION FOR PREVENTING AND TREATING TRANSPLANT REJECTION OR TRANSPLANT REJECTION DISEASES, COMPRISING NOVEL COMPOUND AND CALCINEURIN INHIBITOR

(71) Applicant: THE CATHOLIC UNIVERSITY OF KOREA INDUSTRY-ACADEMIC COOPERATION FOUNDATION, Seoul (KR)

(72) Inventors: Mi-La Cho, Seoul (KR); Dong-Yun Shin, Seoul (KR); Jong-Young Choi, Seoul (KR); Chul-Woo Yang, Seoul (KR); Sung-Hwan Park, Seoul (KR); Seon-Yeong Lee, Seoul (KR); Min-Jung Park, Seoul (KR); Joo-Yeon Jhun, Seoul (KR); Se-Young Kim, Seoul (KR); Hyeon-Beom Seo, Seoul (KR); Jae-Yoon Ryu, Seoul (KR); Keun-Hyung Cho, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 626 days.

(21) Appl. No.: 17/290,637

(22) PCT Filed: Nov. 7, 2019

(86) PCT No.: PCT/KR2019/015055
§ 371 (c)(1),
(2) Date: Apr. 30, 2021

(87) PCT Pub. No.: WO2020/096371
PCT Pub. Date: May 14, 2020

(65) Prior Publication Data
US 2022/0031637 A1    Feb. 3, 2022

(30) Foreign Application Priority Data
Nov. 7, 2018    (KR) .......................... 10-2018-0136107

(51) Int. Cl.
*A61K 31/155*    (2006.01)
*A61K 31/436*    (2006.01)
*A61K 38/13*    (2006.01)
*A61P 37/06*    (2006.01)

(52) U.S. Cl.
CPC ........... *A61K 31/155* (2013.01); *A61K 31/436* (2013.01); *A61K 38/13* (2013.01); *A61P 37/06* (2018.01)

(58) Field of Classification Search
CPC ........................... A61K 31/155; A61K 31/436
USPC ................................................... 514/291, 635
See application file for complete search history.

(56) References Cited

U.S. PATENT DOCUMENTS

| | | |
|---|---|---|
| 8,637,038 B2 | 1/2014 | Taylor et al. |
| 10,016,376 B2 | 7/2018 | Cho et al. |
| 10,100,006 B2 | 10/2018 | Cho et al. |
| 10,369,121 B2 | 8/2019 | Cho et al. |
| 2012/0263737 A1 | 10/2012 | Taylor et al. |
| 2017/0114008 A1 | 4/2017 | Cho et al. |
| 2017/0333370 A1 | 11/2017 | Cho et al. |
| 2017/0348256 A1 | 12/2017 | Cho et al. |
| 2018/0118668 A1 | 5/2018 | Cho et al. |
| 2019/0328685 A1 | 10/2019 | Cho et al. |

FOREIGN PATENT DOCUMENTS

KR    10-2019-0045513 A    5/2019

*Primary Examiner* — Raymond J Henley, III
(74) *Attorney, Agent, or Firm* — Vorys, Sater, Seymour and Pease LLP; Mih Suhn Koh

(57) ABSTRACT

The present invention relates to a composition for preventing or treating transplantation rejection or a transplantation rejection disease, comprising a novel compound and a calcineurin inhibitor. A co-administration of the present invention 1) reduces the activity of pathogenic Th1 cells or Th17 cells, 2) increases the activity of Treg cells, 3) has an inhibitory effect against side effects, such as tissue damage, occurring in the sole administration thereof, 4) inhibits various pathogenic pathways, 5) inhibits the cell death of inflammatory cells, and 6) increases the activity of mitochondria, in an in vivo and in vitro allogenic model, a transplantation rejection disease model, a skin transplantation model, and a liver-transplanted patient, and thus inhibits transplantation rejection along with mitigating side effects possibly occurring in the administration of a conventional immunosuppressant alone. Thus, the present invention may be used in the field of pharmaceutics relating to transplantation rejection or various immune disorders possibly occurring after transplantation.

11 Claims, 37 Drawing Sheets

Control of STAT3 signal molecules by SD282/FK506

Restoration and regulation of mitochondrial function by SD282/FK506

COMPOSITION FOR PREVENTING AND TREATING TRANSPLANT REJECTION OR TRANSPLANT REJECTION DISEASES, COMPRISING NOVEL COMPOUND AND CALCINEURIN INHIBITOR

TECHNICAL FIELD

The present invention relates to a composition for preventing and treating transplantation rejection or a transplantation rejection disease comprising a novel compound and a calcineurin inhibitor.

BACKGROUND ART

Immunosuppressants, a pharmaceutical agent that blocks or lowers the humoral or cellular immune responses producing antibodies against antigens, are used to treat is an immune rejection that occurs mainly after organ transplantation or a graft-versus-host disease after bone marrow transplantation. In addition, immunosuppressants are also impotently used for long-term treatment of autoimmune diseases, such as lupus and rheumatoid arthritis; hyperimmune responses such as allergy and atopy; and symptoms of inflammatory diseases.

Currently used immunosuppressants are divided into corticosteroids, antimetabolites, calcineurin inhibitors, mammalian target of rapamycin (mTOR) inhibitors, and antibodies, depending on their mechanism of action. They exhibit immunosuppressive effects by blocking the proliferation or activation of T cells in the immune system at different stages (Dalal, P et al. Int. J. Nephrol. Renovasc. Dis. 3:107-115 (2010)). T cells, which are a major target of immunosuppressants, are produced in the thymus of the human body and differentiated into type 1 helper cells (Th1) mainly involved in cell-mediated immunity or type 2 helper cells (Th2) involved in humoral immunity. It is known that the two T cell groups are in balance so that they are not overactive with each other and that, when the balance is broken, abnormal reactions such as autoimmunity or hypersensitivity occur. In addition, there are known new types of T cells such as immunoregulatory T cells (Treg cells) or Th17 cells that can regulate immune responses. Treg cells, which can modulate the activity of Th1 cells, inhibit the function of abnormally activated immune cells and regulate inflammatory responses. In contrast, Th17 cells secrete IL-17 and maximize inflammatory response signals, thereby accelerating the progression of diseases. Recently, these Treg or Th17 cells have emerged as new targets for immunological diseases, and various studies on an agent for immunomodulatory treatments are being carried out (Wood, K J et al., Nat. Rev. Immunol. 12(6):417-430, 2012; Miossec, P et al., Nat. Rev. Drug Discov. 11(10):763-776, 2012; Noack, M et al., Autoimmun. Rev. 13(6):668-677, 2014).

Meanwhile, transplantation refers to the process of taking cells, tissues, or organs (i.e., grafts) from one individual and transferring them to another individual. The individual who provides the grafts is called as a donor and the individual who receives the grafts is called as a recipient or a host. In the case of transplanted organs, rejection occurs due to an immunological response to the histocompatibility antigens (transplanted antigens) on the cell surface of the grafts. The long-term engraftment of grafts in a recipient who is not immune-suppressed is limited to the case in which histocompatibility is completely or mostly consistent, and thus the genetic relationship between the donor and the recipient is a factor that greatly influences the engraftment period of the grafts. In general, rejections rarely occur in autografts and isografts; however, rejections occur almost in allografts. During the transplantation of tissues or organs, the genetic difference between the donor and the recipient is easily detected by the host immune system, which results in the host's response to the transplanted tissues (host-versus-graft response) and/or the transplanted tissues' response to the host (graft-versus-host response). These facts have been demonstrated by the rejections brought about in tissue and organ transplantations (Nash et al., Blood, 80, 1838-1845, 1992). In addition, there has been reported that rejection of allo-transplanted tissues occurs by T cells activated by an immune response to MHC present on the surface of the transplanted cells (Benichou et al., J. Exp. Med. 175, 305-308, 1992; Benichou et al., J. Immunol. 162, 352-358, 1998; Fangmann et al., J. Exp. Med. 175, 1521-1529, 1992; Lombardi et al., Proc. Acad. Sci. USA, 86, 4190-4194, 1989).

Immunosuppressants that non-specifically inhibit T cells in order to suppress these transplantation rejections or a transplantation rejection disease are generally accompanied by side effects such as cytotoxicity, infections due to lowered immunity, diabetes, tremor, headache, diarrhea, high blood pressure, nausea, and renal dysfunction, and thus have a disadvantage that it is difficult to maintain the long-term treatment effects thereof. Therefore, in order to reduce serious side effects and increase the immunosuppressive treatment effects, there have been tried methods of co-administration or replacement of immunosuppressants having different mechanisms of action, especially in the field of organ transplantation. However, the optimized combination or therapy for co-administrating immunosuppressants is not yet available.

Therefore, there is an urgent need to develop a novel immunosuppressive or immunomodulatory therapy that can reduce side effects of the existing immunosuppressants and improve therapeutic effects thereof; and to discover novel immunosuppressant candidates that are more safe and have fewer side effects.

The present inventors found that co-treatment of the compound SD282 and a calcineurin inhibitor suppresses transplantation rejection; reduces side effects derived from the non-specific inhibition of T cells; and prevent and treat immune diseases that may occur after transplantation, thereby completed the present invention.

DISCLOSURE

Technical Problem

It is an object of the present invention to provide a pharmaceutical composition for preventing or treating transplantation rejection or a transplantation rejection disease, comprising 1) a compound represented by the following formula 1 or a pharmaceutically acceptable salt thereof and 2) a calcineurin inhibitor or a pharmaceutically acceptable salt thereof as active ingredients.

In addition, it is another object of the present invention to provide a pharmaceutical composition for immunosuppression after transplantation, comprising 1) a compound represented by the following formula 1 or a pharmaceutically acceptable salt thereof and 2) a calcineurin inhibitor or a pharmaceutically acceptable salt thereof as active ingredients.

Technical Solution

In order to achieve the above-mentioned objects of the present invention, the present invention provides a pharmaceutical composition for preventing or treating transplantation rejection or a transplantation rejection disease, comprising 1) a compound represented by the following formula 1 or a pharmaceutically acceptable salt thereof and 2) a calcineurin inhibitor or a pharmaceutically acceptable salt thereof as active ingredients.

In addition, the present invention provides a pharmaceutical composition for immunosuppression after transplantation, comprising 1) a compound represented by the following formula 1 or a pharmaceutically acceptable salt thereof and 2) a calcineurin inhibitor or a pharmaceutically acceptable salt thereof as active ingredients.

Advantageous Effects

The co-administration of the compound SD282 and a calcineurin inhibitor according to the present invention 1) reduces the activity of pathogenic Th1 cells or Th17 cells, 2) increases the activity of Treg cells, 3) has an inhibitory effect against side effects, such as tissue damage, occurring in the sole administration thereof, 4) inhibits various pathogenic pathways, 5) inhibits the cell death of inflammatory cells, and 6) increases the activity of mitochondria, in an in vivo or in vitro allogenic model, a transplantation rejection disease model, a skin transplantation model, and a liver-transplanted patient, and thus inhibits transplantation rejection along with mitigating side effects possibly occurring in the administration of a conventional immunosuppressant alone. Therefore, the present invention may be used in the field of pharmaceutics relating to transplantation rejection or various immune disorders possibly occurring after transplantation.

BEST MODE FOR CARRYING OUT THE INVENTION

Figure 1A:
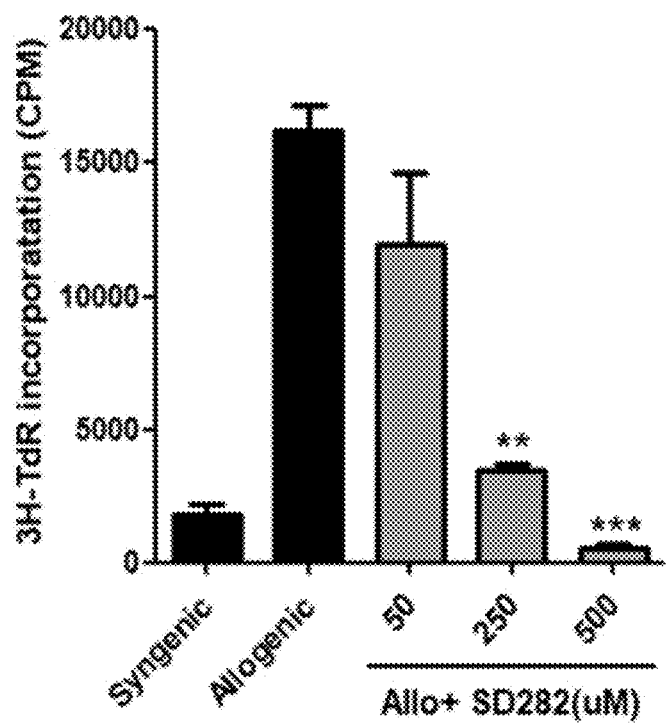
FIG. 1 is the results obtained by confirming the T cell proliferation responses according to the co-treatment of SD282+FK506 in an allogenic transplantation mouse model by the 3H-thymidine incorporation assay.

The present invention provides a pharmaceutical composition for preventing or treating transplantation rejection or a transplantation rejection disease, comprising 1) a compound represented by the following formula 1 (hereinafter, referred to as 'the compound SD282') or a pharmaceutically acceptable salt thereof and 2) a calcineurin inhibitor or a pharmaceutically acceptable salt thereof as active ingredients.

The co-administration of the compound SD282 and a calcineurin inhibitor in the present invention 1) reduces the activity of pathogenic Th1 cells or Th17 cells, 2) increases the activity of Treg cells, 3) has an inhibitory effect against side effects, such as tissue damage, occurring in the sole administration thereof, 4) inhibits various pathogenic pathways, 5) inhibits the cell death of inflammatory cells, 6) increases the activity of mitochondria, and 7) decreases cell migration, in an in vivo or in vitro allogenic model, a transplantation rejection disease model, a skin transplantation model, and a liver-transplanted patient, and thus effectively inhibits various types of transplantation rejection along with mitigating side effects occurring in the administration of a conventional immunosuppressant alone.

The weight ratio of the compound of Formula 1 and the calcineurin inhibitor according to the present invention may be in a range of 1:1 to 5000:1, preferably 1:1 to 2000:1, 1:1 to 1000:1, 1:1 to 500:1, 1:1 to 300:1, 1:1 to 200:1, 1:1 to 100:1, 1:1 to 50:1, 1:1 to 10:1, 1:1 to 5:1, but are not limited thereto.

As used herein, the term "transplantation rejection" refers to a reaction that, recognizing the transplanted tissue as non-self after the transplantation, the recipient's immune system attacks and removes the transplanted tissue or organ. The most important factor involved in transplant rejection is the major histocompatibility complex (MHC), and the minor histocompatibility complex is also known to be related. Both cell-mediated immune response and humoral immune response are involved in the rejection reaction. Cell-mediated reactions are caused by CD4 T cell-type II MHC molecules or CD8 T cell-type I MHC molecules through the encounter of the recipient's lymphocytes with the donor's MHCs. Activated T cells secrete cytokines, increase blood vessel permeability, and bring about invasion of monocytes such as macrophages, thereby resulting in damage to microvessels, tissue ischemia, and destruction of transplanted tissues and cells.

As used herein, the term "the compound SD282", which is known in Korean Patent No. 10-1613371, refers to the compound represented by the following formula 1 which may include a pharmaceutically acceptable salt thereof.

<Formula 1>

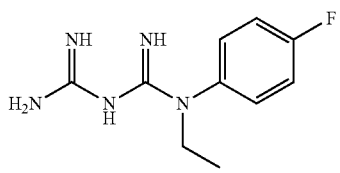

As used herein, the term "calcineurin inhibitor" refers to a kind of immunosuppressants which inhibits the production of IL-2 by interfering with the formation of mRNA in T-lymphocytes, including cyclosporine (the left compound in Formula 2) and FK-506 (tacrolimus; the right compound in Formula 2), representatively.

<Formula 2>

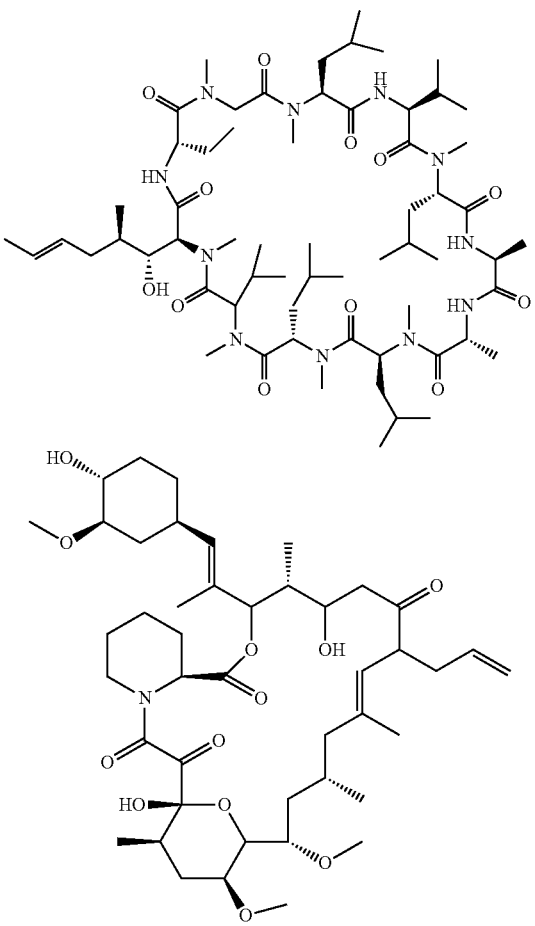

As used herein, the term "FK-506" refers to the compound isolated from Streptomyces tsukubaensis. Although FK-506 is structurally different from cyclosporine, it inhibits T-lymphocytes to exhibit an immunosuppressive function, similarly to the mechanism of action of cyclosporine. FK-506 is known to have 10 to 100 times the efficacy of cyclosporine.

Since calcineurin is expressed not only in T cells of the immune system but also in other cells and tissues, the inhibitory action of cyclosporine or tacrolimus against calcineurin causes various side effects besides immunosuppression (Liu, E H et al, Nat Immunol 8(1):25-30, 2007). The side effects of immunosuppressants have serious effects on the long-term stable and successful organ transplantation and the survival rates of transplantation-received patients. Furthermore, said side effects will be big problems in the treatment of diseases other than organ transplantations requiring immunosuppression. Among the side effects of calcineurin immunosuppressants, acute and chronic nephrotoxicity is particularly important (Naesens, M et al, Clin J Am Soc Nephrol 4(2):481-508, 2009). The nephrotoxicity induced by calcineurin immunosuppressants shows histological changes in the kidney tissues, such as vacuolization in tubules, interstitial fibrosis, and vitrification of arterioles; and decreases in renal function, such as decreases in effective renal blood flow and glomerular filtration rate.

In an embodiment of the present invention, the compound SD282 was co-treated in combination with the calcineurin immunosuppressant FK-506, so as to reduce the side effects of said calcineurin immunosuppressant, i.e., the side effects that it inhibits Treg cells and increases pathogenic Th17 cells. As the results thereof, it has been confirmed that the co-treatment alleviates the side effects of calcineurin immunosuppressants by increasing Treg cells and decreasing pathogenic Th17 cells in vivo and in vitro.

The transplantation rejection is one or more transplantation rejections selected from the group consisting of cells, blood, tissues and organs. Preferably, the transplantation rejection is one or more selected from the group consisting of bone marrow transplantation rejection, heart transplantation rejection, corneal transplantation rejection, bowel transplantation rejection, liver transplantation rejection, lung transplantation rejection, pancreas transplantation rejection, kidney transplantation rejection, and skin transplant rejection, but not limited thereto.

The transplantation rejection disease in the present invention includes graft-versus-host disease (GVHD), but not limited thereto if a disease is related to transplantation rejection, by treatment with SD282 or FK-506 alone or in combination.

In addition, the present invention may be used for treating an immune disease after transplantation. Said immune disease may include an autoimmune disease or an inflammatory disease.

The non-response of a living body to self-antigens is referred to as immunologic unresponsiveness or tolerance. As used herein, the term "autoimmune disease" refers to a disease caused during the phenomenon of attacking the one's own tissues by bringing about an immune response against self-antigens due to a problem in inducing or maintaining such self-tolerance.

As used herein, the term "inflammatory disease" refers to the diseases caused by inflammatory substances (inflammatory cytokines) such as TNF-α (tumor necrosis factor-α), IL-1 (interleukin-1), IL-6, prostaglandin, leukotriene or nitric oxide (NO), which are secreted from immune cells, e.g., macrophage, according to excessive enhancement of the immune system due to harmful stimuli such as inflammation-inducing factors or irradiation.

The immune diseases may include rheumatoid arthritis, Behcet's disease, polymyositis or dermatomyositis, autoimmune cytopenia, autoimmune myocarditis, atopic dermatitis, asthma, primary cirrhosis, dermatomyositis, Goodpasture's syndrome, autoimmune meningitis, Sjogren's syndrome, lupus, Addison's disease, alopecia areata, ankylosing myelitis, autoimmune hepatitis, autoimmune mumps, Crohn's disease, insulin-dependent diabetes, dystrophic epidermolysis bullosa, epididymitis, glomerulonephritis, Graves' disease, Guillain-Barre syndrome, Hashimoto's disease, hemolytic anemia, multiple sclerosis, myasthenia gravis, pemphigus vulgaris, psoriasis, rheumatic fever, sarcoidosis, scleroderma, spondyloarthropathy, thyroiditis, vasculitis, vitiligo, myxedema, pernicious anemia, mitochondria-related syndrome and ulcerative colitis, but not limited thereto.

The composition may inhibit the proliferation of T cells. And, the composition may decrease a differentiation of undifferentiated T cells to Th1 cells or Th17 cells; or an activity of Th1 cells or Th17 cells In addition, the composition increases a differentiation of undifferentiated T cells to Treg cells and an activity of Treg cells, but not limited thereto.

According to the recent studies on the differentiation of Th1 cells, it has been found that there are existed a new population, i.e., immunoregulatory T cells (Treg cells) modulating the activity of Th1 cells; and thus, there are emerging researches on the treatment of immune diseases using the same. Since the Treg cells have a characteristic to suppress the function of abnormally activated immune cells to control inflammatory responses, immune diseases can be treated through increasing the activity of Treg cells.

In addition to the Treg cells, Th17 cells are formed during the differentiation as another group. Th17 cells are known to be formed during the differentiation of undifferentiated T cells, according to similar differentiation processes to those of Treg cells. That is, the differentiations to Treg cells and Th17 cells are commonly made in the presence of TGF-β. However, the differentiation to Treg cells does not require IL-6, while the differentiation to Th17 cells is made in the presences of both TGF-β and IL-6. The differentiated Th17 cells are characterized by the secretion of IL-17.

It has been found that Th17 cells, different from Treg cells, are involved in the first line of the inflammatory response shown in immune diseases to maximize the signals of the inflammatory response, thereby accelerating the progression of the disease. Therefore, in case of the autoimmune diseases that are not controlled by Treg cells, developments of a therapeutic agent of immune diseases for targeting the inhibition of Th17 cell activity have been significantly highlighted.

As used herein, the term "T cells", cells involved in an immune response, refers to a T cell population that expresses specific cell surface markers.

Human has various histocompatibility antigens, e.g., Class I antigens such as HLA-A, —B, and —C; and Class II antigens such as HLA-DR, -DP, and -DQ. The biological function of these antigens is to deliver an antigen to T lymphocytes. The Class I antigens are expressed in most of nucleated cells; and the antigens delivered thereby are recognized by CD8+ cytotoxic T lymphocytes. The Class II antigens are expressed in dendritic cells known as antigen-presenting cells, B lymphocytes, activated T lymphocytes, macrophages, etc.; and deliver antigens to CD4+ T lymphocytes. The T lymphocytes recognize the antigens through binding the antigens delivered to T lymphocytes to the receptors thereon. In the course of the transplantation, the T lymphocytes recognize the histocompatibility antigens derived from the other person in higher frequency than one's own histocompatibility antigens. 1% to 10% of all T lymphocytes in a donors or a patient recognizes the histocompatibility antigens derived from the patient or the donor; and proliferate in response thereto, thereby causing a series of immune responses, which is called as "alloresponse".

The pharmaceutical composition of the present invention may further comprise an adjuvant. Any of the adjuvants known in the art may be used without limitation. For example, Freund's complete adjuvant or incomplete adjuvant may be further comprised so as to increase its immunity.

The pharmaceutical composition according to the present invention may be prepared in a form in which the active ingredients are incorporated into a pharmaceutically acceptable carrier. The pharmaceutically acceptable carrier includes carriers, excipients, and diluents conventionally used in the pharmaceutical field. The pharmaceutically acceptable carriers that can be used in the pharmaceutical composition of the present invention may be lactose, dextrose, sucrose, sorbitol, mannitol, xylitol, erythritol, maltitol, starch, acacia gum, alginate, gelatin, calcium phosphate, calcium silicate, cellulose, methyl cellulose, polyvinylpyrrolidone, water, methyl hydroxybenzoate, propyl hydroxybenzoate, talc, magnesium stearate and mineral oil, but not limited thereto, The pharmaceutical composition of the present invention may be formulated and used in the form of oral dosage forms such as powders, granules, tablets, capsules, suspensions, emulsions, syrups, aerosols, etc., external preparations, suppositories, or sterile injectable solutions, according to conventional methods.

In formulating the composition of the present invention, it may be prepared using conventionally used diluents or excipients, such as fillers, extenders, binders, wetting agents, disintegrating agents, and surfactants. Solid formulations for oral administration include tablets, pills, powders, granules, capsules, etc., which may be prepared by mixing active ingredients with at least one excipient such as starch, calcium carbonate, sucrose, lactose, gelatin and the like. In addition to the excipients, lubricants such as magnesium stearate and talc may also be used. Liquid formulations for oral administration include suspensions, liquid solutions, emulsions, syrups, etc., which may comprise various excipients, such as wetting agents, sweeteners, fragrances, and preservatives, as well as conventionally used diluents such as water and liquid paraffin. Formulations for parenteral administration include sterile aqueous solutions, non-aqueous solutions, suspensions, emulsions, lyophilized formulations, and suppositories. As a non-aqueous solvent or a suspending agent, propylene glycol, polyethylene glycol, vegetable oils such as olive oil, and injectable esters such as ethyl oleate may be used. As a base for suppositories, witepsol, Tween 61, cacao butter, laurin butter, glycerogelatin, and the like may be used.

The pharmaceutical composition according to the present invention may be administered to a subject via various routes. Any modes of administration can be expected and therefore said composition may be administered through oral administration, intravenous injection, intramuscular injection, subcutaneous injection, and intraperitoneal injection.

The dosage of the pharmaceutical composition according to the present invention is selected in consideration of the subject's age, weight, sex, and physical condition. It is clear that the concentrations of the active ingredients in the pharmaceutical composition may be selected in various ways depending on the subject. Preferably, the active ingredients may be present in a concentration ranging from 0.01 to 5,000 µg/ml in the pharmaceutical composition. When the concentration is less than 0.01 µg/ml, pharmacological activity may not appear; and when the concentration exceeds 5,000 µg/ml, toxicity to the human body may occur.

The pharmaceutically effective amount of the calcineurin inhibitor comprised as an active ingredient in the pharmaceutical composition of the present invention is 1 to 5 mg/day/kg body weight for cyclosporine, 0.01 to 0.1 mg/day/kg body weight for tacrolimus, and 5 to 35 mg/day/kg body weight for metformin. However, the pharmaceutically effective amount may be appropriately changed according to various factors such as the disease and its severity, the patient's age, weight, health condition, sex, administration route, and treatment period.

In addition, the present invention provides a composition for immunosuppression after transplantation, comprising 1) a compound represented by the formula 1 (hereinafter, referred to as 'the compound SD282') or a pharmaceutically acceptable salt thereof and 2) a calcineurin inhibitor or a pharmaceutically acceptable salt thereof as active ingredients.

In addition, the present invention provides a method for decreasing a differentiation of undifferentiated T cells to Th1 cells or Th17 cells or an activity of Th1 cells or Th17 cells, by treating undifferentiated T cells with 1) a compound represented by the formula 1 or a pharmaceutically acceptable salt thereof and 2) a calcineurin inhibitor or a pharmaceutically acceptable salt thereof in vitro.

In addition, the present invention provides a method for increasing a differentiation of undifferentiated T cells to Treg cells and an activity of Treg cells, by treating undifferentiated T cells with 1) a compound represented by the formula 1 or a pharmaceutically acceptable salt thereof and 2) a calcineurin inhibitor or a pharmaceutically acceptable salt thereof in vitro.

In addition, the present invention provides a method for preventing or treating transplantation rejection or a transplantation rejection disease, comprising administering pharmaceutically effective amounts of 1) a compound represented by the formula 1 or a pharmaceutically acceptable salt thereof and 2) a calcineurin inhibitor or a pharmaceutically acceptable salt thereof as active ingredients to a subject in need thereof. In addition, the present invention provides a method for immunosuppression after transplantation, comprising administering pharmaceutically effective amounts of 1) a compound represented by the formula 1 or a pharmaceutically acceptable salt thereof and 2) a calcineurin inhibitor or a pharmaceutically acceptable salt thereof as active ingredients to a subject in need thereof.

The pharmaceutical composition of the present invention is administered in a therapeutically effective amount or in a pharmaceutically effective amount. The term "pharmaceutically effective amount" refers to an amount sufficient to treat a disease with a reasonable benefit/risk ratio applicable to medical treatment. The effective dose level may be determined according to various factors, including types and severity of the individual, age, sex, activity of the drugs, sensitivity to the drugs, administration time, administration routes and excretion rates, treatment duration, co-used drugs, and other factors well known in the medical field.

The invention present will be described in more detail in reference to the following examples. However, these examples are intended to illustrate the present invention more specifically, but the scope of the present invention is not intended to be limited to these examples.

MODE FOR CARRYING OUT THE INVENTION

Example 1. Experimental Method 1-1. In Vitro Syngeneic Graft Transplantation or Allogenic Transplantation Models CD4+ T cells derived from a normal recipient (Balb/c, responder) ($2\times10^5$ cells) were injected into each well of a 96-well round bottom plate, in vitro. Thereafter, for syngenic transplantation, normal recipient-derived T cell-removed splenocytes ($2\times10^5$ cells), which had been irradiated with radiation, were added to each of the wells, followed by culturing under mixing. For allogenic transplantation, donor (C57BL/6, stimulator)-derived T cell-removed splenocytes were added to each of the wells, followed by culturing under mixing.

1-2. Acute Graft Versus Host Disease (aGVHD) Animal Models

For preparing an aGVHD model, the recipient mouse Balb/c (H-2k/d) was subject to total body irradiation (TBI) in 800 cGy. Hematopoietic stem cells and splenocytes were isolated from the femur and tibia of the donor mouse C57BL/6 (H-2k/b). The hematopoietic stem cells (5×10⁶) and splenocytes (1×10⁷) were transplanted into the recipient mice Balb/c (H-2k/d). After the onset of aGVHD, each drug was orally administered to analyze the disease control effects.

1-3. Skin Transplantation Animal Models

For preparing a skin transplantation animal model, the recipient mouse Balb/c (H-2k/d) was injected with drugs from 3 days before skin transplantation. An incision of 1 cm or less was prepared from the skin of the donor mouse C57BL/6 (H-2k/b), straightened so that the tip thereof was not curled, and then transplanted into BALB/C mice. Progress after the transplantation was observed to determine any rejection. The injection concentrations of each drug were 50 mg/kg for SD282 and 10 mg/kg for FK506.

Example 2. Evaluation on T Cell Proliferations According to the Treatment of SD282 Alone, FK506 Alone or in Combination Thereof in Mouse Cells In order to evaluate T cell proliferations according to the treatment with SD282 alone, FK506 alone or in combination thereof, the untreated syngenic group and the untreated allogenic group of Example 1-1 were used as controls. The allogenic model was treated with 50, 250 and 500 μM of SD282 alone or 1 and 5 nM of FK506 alone. And, FK506 (1 and 5 nM) and SD282 (250 μM) were treated in combination, respectively. After the treatments, each group was cultured for 4 days and then alloresponses were evaluated by observing the T cell proliferations of the cultured cells, according to the 3H-thymidine incorporation method, the CFSE assay method, or the flow cytometry method.

Figure 1B:
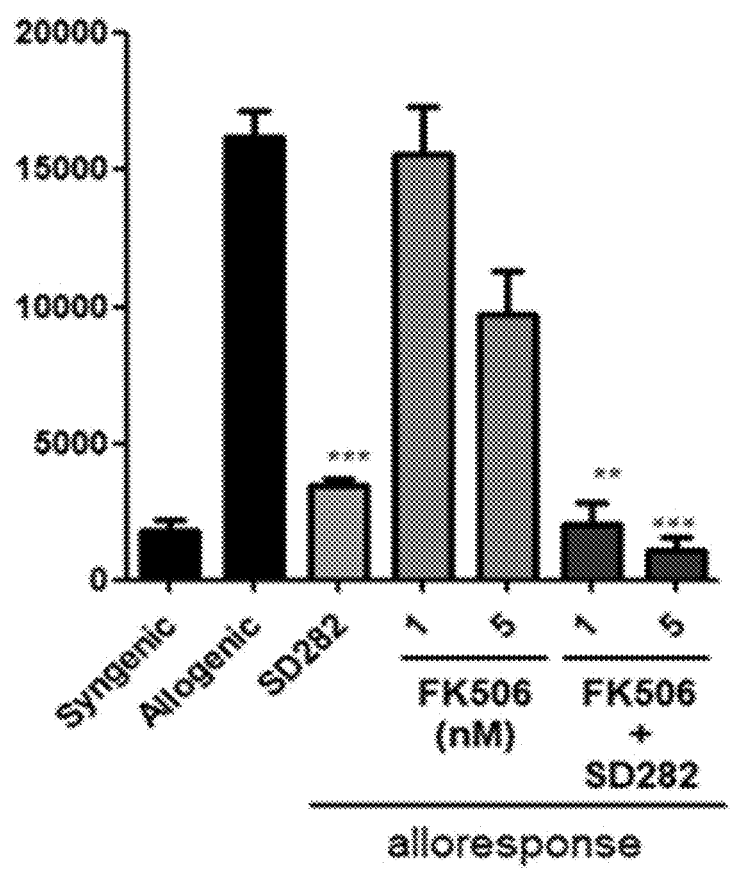

As shown in FIG. 1a, the T cell proliferation was not inhibited in the untreated allogenic group, but it was confirmed that the T cell proliferation was significantly inhibited when 250 μM or more of SD282 was treated alone. In addition, as shown in FIG. 1b, it was confirmed that the inhibition in the group treated with FK506 alone was not effective, which is similar to that of the untreated group. However, it was confirmed that the treatment of SD282 and FK506 in combination significantly inhibited the proliferation of allogenic T cells.

Figure 2A:
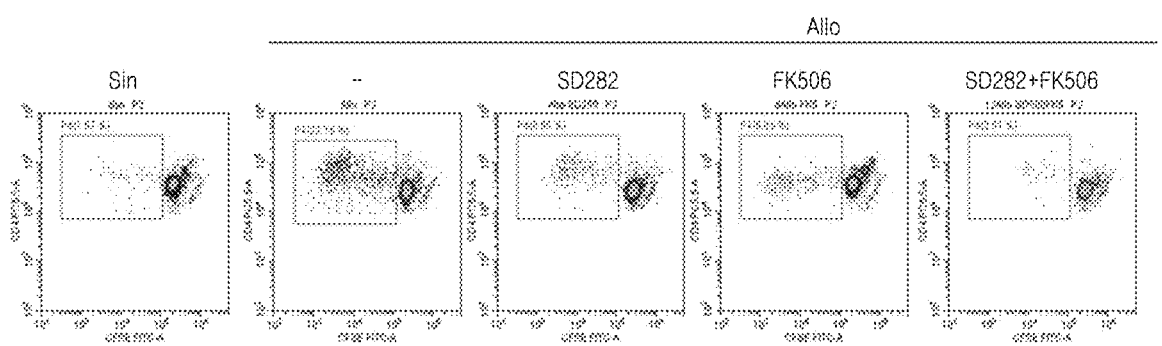
FIG. 2(A) is the results obtained by confirming the T cell proliferation responses according to the co-treatment of SD282+FK506 in an allogenic transplantation mouse model by the flow cytometric analysis.
Figure 2B:
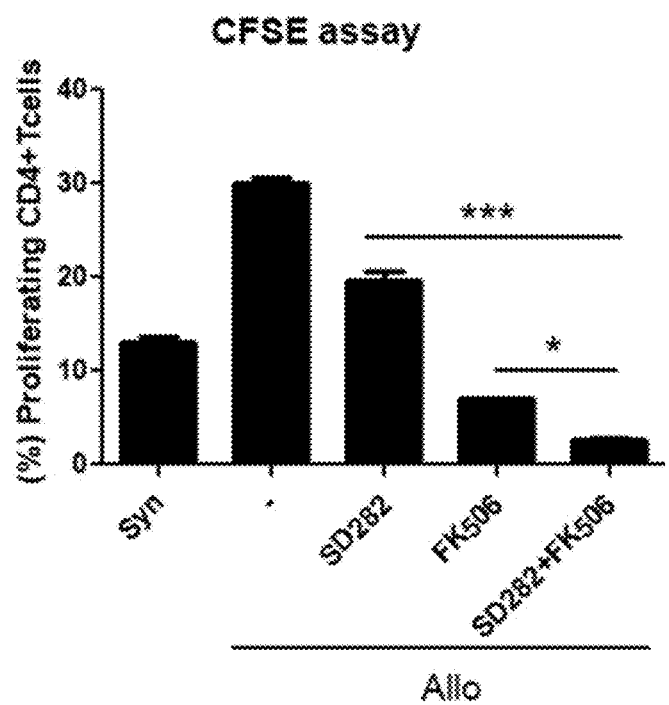
FIG. 2(B) is the graphical results thereof.

In addition, as shown in FIG. 2a and FIG. 2b, the T cell proliferation was not inhibited in the untreated allogenic group, but it was confirmed that the T cell proliferation was inhibited in the group treated with SD282 alone or in the group treated with FK506 alone and that the T cell proliferation was more effectively inhibited in the group treated with SD282 and FK506 in combination.

In addition, in order to evaluate the synergistic effect according to the treatment of SD282 and FK506 in combination, the Combination Index (CI) value (drug treatment) was calculated. The CI value was obtained by the following equation. A value of 1 or less means that there is a synergistic effect between the combination of two drugs, and a value of 1 or more means that there is an antagonistic effect between the combination of two drugs.

As a result thereof, it was confirmed that the CI value according to the treatment of SD282 and FK506 in combination of the present invention was 0.6 (i.e., less than 1), showing excellent synergistic effect.

$CI=(D \text{ comb})1/(D \text{ alone})1+(D \text{ comb})2/(D \text{ alone})2$ [Equation 1]

Example 3. Evaluation on the Activity of Th17 Cells or Treg Cells According the Treatment of SD282 and FK506 in Combination in Mouse Cells 3-1. Evaluation on Inhibitory Effects Against Pathogenic Th17 Cells The T cell response regulates the activity of Th17 (T helper 17 cell)/IL-17 (Interleukin 17) and IL-17 is classified as an inflammatory cytokine. In Example 2, it was confirmed that T cells were effectively inhibited by the treatments with SD282 and FK506 alone or in combination. We also evaluated inhibitory activity against inflammatory cytokines according to the treatments with SD282 and FK506 alone or in combination. The untreated syngenic group and the untreated allogenic group of Example 1-1 were used as controls. The allogenic models were treated with 50, 250 and 500 μM of SD282 alone or 1 and 5 nM of FK506 alone. And, FK506 (1 and 5 nM) and SD282 (250 μM) were treated in combination, respectively. After the treatments, each group was cultured for 4 days and then stimulated with anti-CD3 (0.1 μg/ml). The inhibitory efficacy against IL-17+CD4+ T cells and IL-17 was evaluated by analyzing the cultured Th17 cells according to the ELISA method; and the proliferation of Fox3+ Treg cells was evaluated through the analysis of Treg cells.

Figure 3:
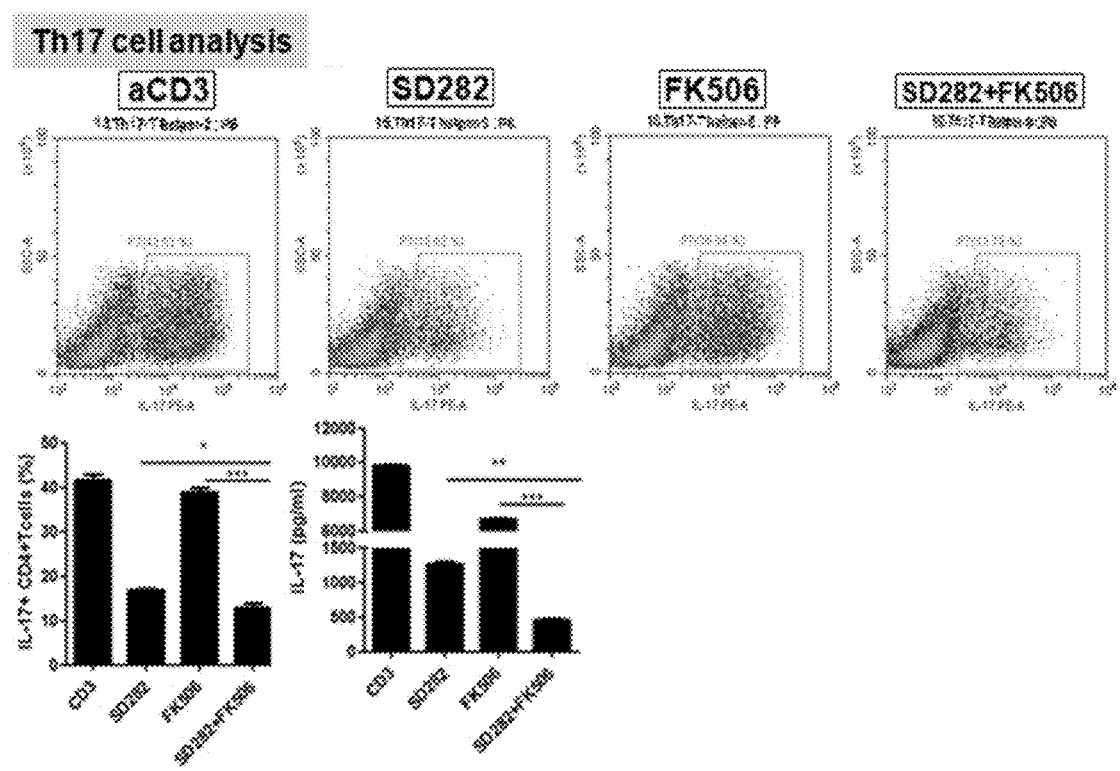
FIG. 3 is the results obtained by confirming the inhibitory effects against the activity of pathogenic Th17 cells, by the co-treatment of SD282+FK506 in an allogenic transplantation mouse model.

As shown in FIG. 3, it was confirmed that the group treated with FK506 alone did not effectively inhibit the proliferation of pathogenic Th17 cells, which is similar to that of the control group, i.e., the anti-CD3 treatment group, which means that the treatment of FK506 alone did not effectively inhibit the activity of the inflammatory cytokine IL-17. On the other hand, it was confirmed that the IL-17+ CD4+ T cells (%) and the activity of IL-17 were inhibited by the treatment with each SD282 and Fk506 alone, and more significantly inhibited by the treatment with the combination thereof.

3-2. Evaluation on Increases in the Treg Activity

The allogenic models of Example 1-1 were treated with 20 and 500 μM of SD282 alone or 1 and 5 nM of FK506 alone. And, FK506 (1 and 5 nM) and SD282 (250 μM) were treated in combination, respectively. The isolated T cells were cultured for 4 days under the condition of Th17 cell differentiation so as to induce the differentiation to Th17 cells. Thereafter, in order to evaluate whether Treg cell activity was also induced in each of the treatment groups under the condition of Th17 cell differentiation, Foxp3 Treg cells were analyzed by flow cytometry and allogenic reactions thereof were evaluated.

Figure 4:
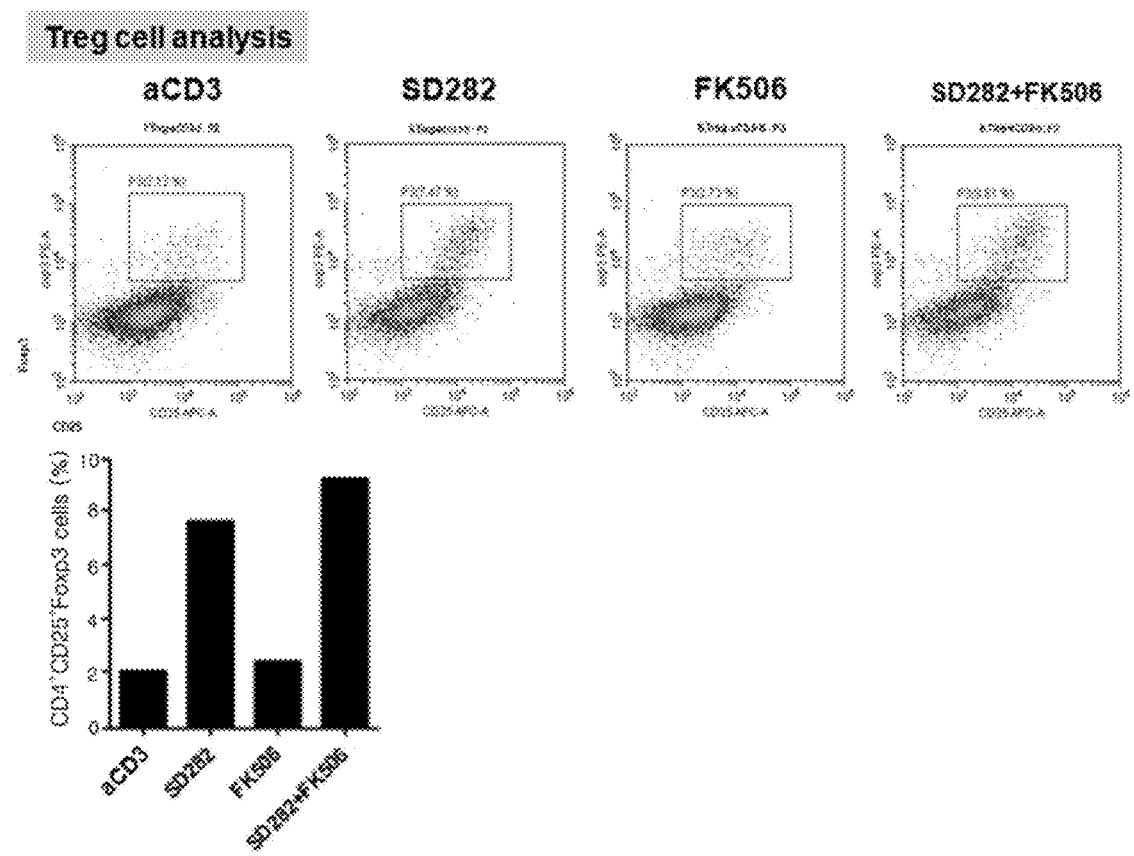
FIG. 4 is the results obtained by confirming the increasing effects of the activity of Treg cells, by the co-treatment of SD282+FK506 in an allogenic transplantation mouse model.

As shown in FIG. 4, it was confirmed that the group treated with FK506 alone did not increase the proliferation of Treg cells, which is similar to that of the control group, i.e., the anti-CD3 treatment group. On the other hand, it was confirmed that the groups treated with SD282 alone, Fk506 alone, and the combination of SD282 and Fk506 significantly increased the Treg cells.

Therefore, it was confirmed that the co-administration has not only the effect reducing the activity of pathogenic Th17 cells but also the effect increasing the activity of Treg cells.

Figure 5:
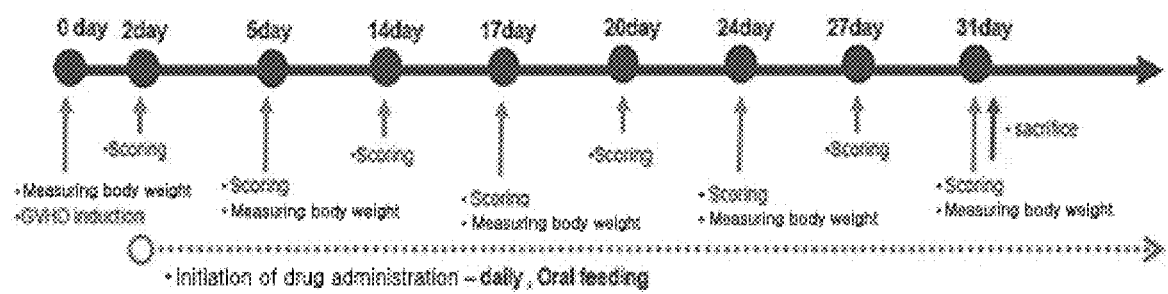
FIG. 5 is the experimental method for confirming effects of the co-administration in a graft versus host disease (GVHD) animal model.

Example 4. Evaluation on Treatment Effects According to the Treatment of SD282 and FK506 in Combination in an Acute Graft Versus Host Disease (GVHD) Animal Model 4-1. Changes in GVHD Mouse Models According to the Treatment of SD282 and FK506 in Combination The experiments as shown in FIG. 5 were performed on the GVHD animal model of Example 1-2. After the occurrence of GVHD, we administered 50 or 100 mg/kg of SD282 alone or 10 mg/kg of FK506 alone thereto. And, 10 mg/kg of FK506 and 50 or 100 mg/kg of SD282 were orally co-administrated thereto, respectively. Thereafter, we evaluated the body weight (g), the change rate of body weight (%), and the score of the change rate of body weight (%) in the GVHD mouse models.

Figure 6:
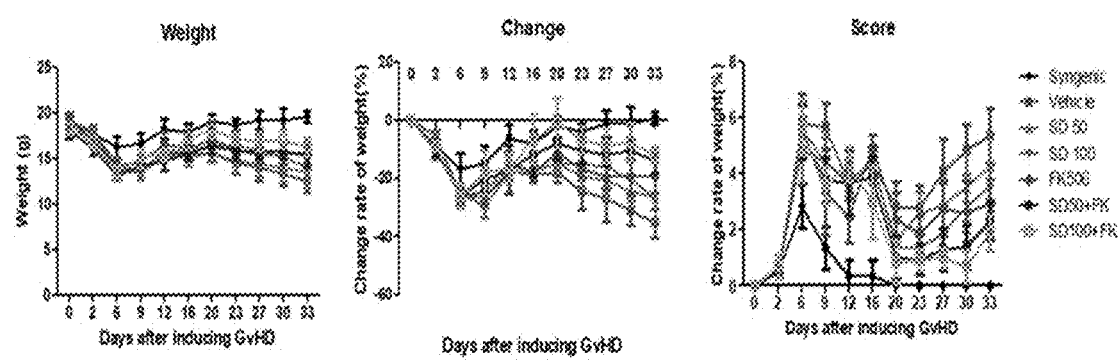
FIG. 6 is the results obtained by confirming the treatment effects of GVHD, by the co-treatment of SD282 and FK506 in a graft versus host disease (GVHD) animal model.

As shown in FIG. 6, in the GVHD mouse model group treated with SD282 and FK506 in combination, the normal body weight was maintained. And also, it was confirmed that the loss rate of body weight (%) according to the induction of the transplantation rejection by allogenic transplantation was remarkably low, in comparison with those of the group treated with SD282 alone or FK506 alone; and that the change rate of body weight and the score thereof (%) were similar to those of the syngenic group. Therefore, it was confirmed that the GVHD treatment effect of the drugs exists in the GVHD mouse model.

In addition, we evaluated the disease scores of the group administered with 20, 50 or 100 mg/kg of SD282 alone, the group administered with 2 or 10 mg/kg of FK506 alone, and the group administered with the combination of 50 mg/kg of SD282+2 or 10 mg/kg of FK506, in the GVHD mouse model.

Figure 7A:
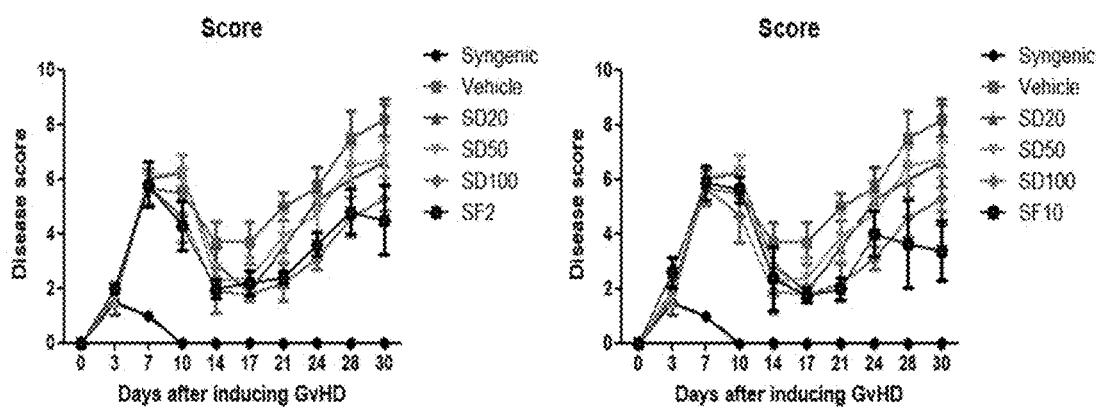
FIG. 7 is the results obtained by confirming the treatment effects of GVHD, by the co-treatment of SD282 and FK506 in a graft versus host disease (GVHD) animal model.
Figure 7B:
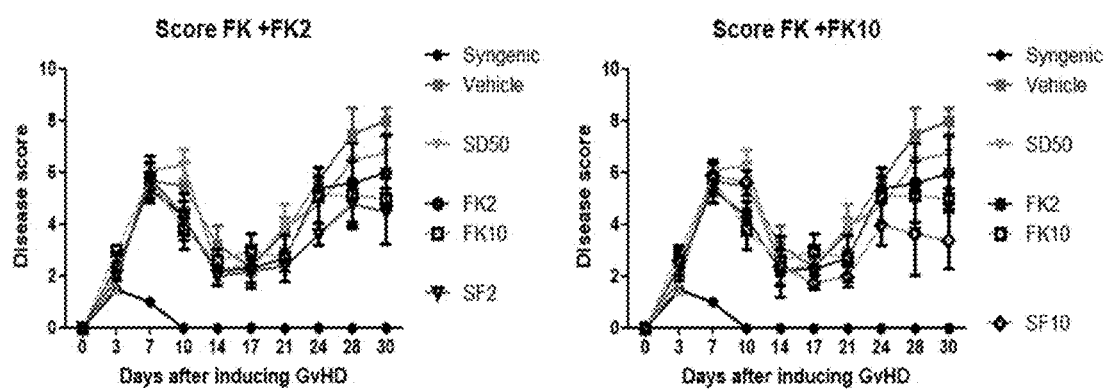

As shown in FIG. 7a, it was confirmed that the disease score of the group administered with the combination thereof was lower in comparison with those of the groups administered with SD282 alone. And also, as shown in FIG. 7b, it was confirmed that the disease score of the group administered with the combination thereof was lower in comparison with those of the groups administered with FK506 alone.

In addition, as a result of calculating the CI value according to Equation 1, it was confirmed that the CI value according to the treatment of SD282 and FK506 in combination was 0.7, showing synergistic effect.

4-2. Evaluation on Inhibitions Against Tissue Cell Invasion and Tissue Damage According to the Treatment of SD282 and FK506 in Combination The experiments as shown in FIG. 5 were performed on the GVHD animal model of Example 1-2. After the occurrence of GVHD, we treated 50 mg/kg of SD282 alone or 10 mg/kg of FK506 alone. And, 10 mg/kg of FK506 and 50 mg/kg of SD282 were orally co-administered thereto, respectively. Thereafter, the therapeutic effects of GVHD were evaluated through the histological scores, indicating the severity of the disease, in the skin, lung, liver, large intestine, small intestine, and cecum.

Figure 8A:
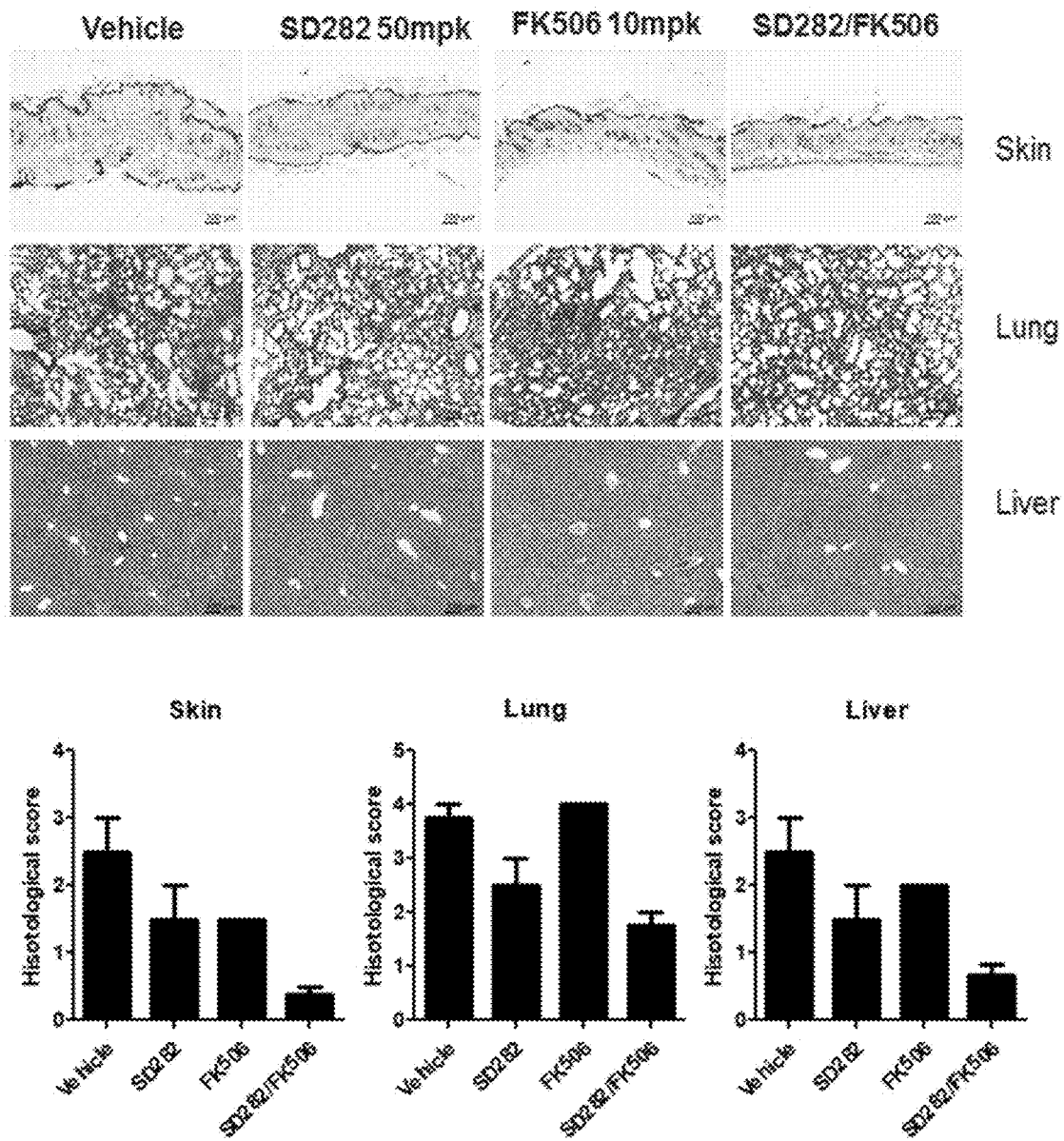
FIG. 8 is the results obtained by confirming the inhibitory effects against organ damages, by the co-treatment of SD282 and FK506 in a graft versus host disease (GVHD) animal model (FIG. 8a: lung, liver, skin.
FIG. 8b: large intestine, small intestine, cecum).
Figure 8B:
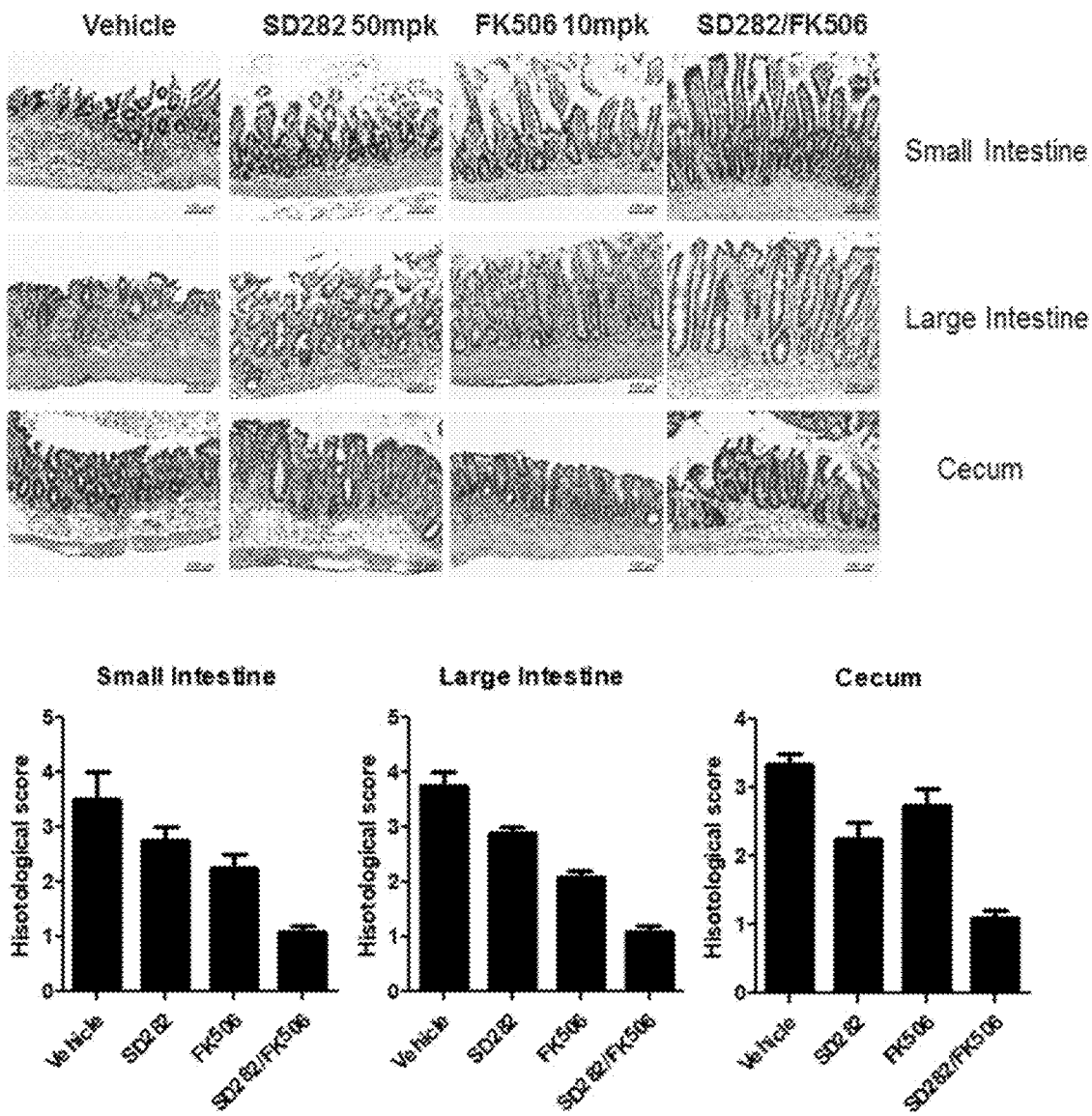

As shown in FIG. 8a, it was confirmed that the histological scores in the skin, lungs and liver were lowered in the group treated with SD282 and FK506 in combination, compared to the group treated with FK506 alone. In addition, as shown in FIG. 8b, it was confirmed that the histological scores of the small intestine, large intestine, and cecum therein were also lowered.

Therefore, it was observed that the invasion of inflammatory cells into the tissue and the tissue damage caused by GVHD were inhibited in the group treated with SD282 and FK506 in combination.

4-3. Evaluation on the Activities of Th17 Cells and Th1 Cells According to the Treatments of SD282 Alone, FK506 Alone, or in Combination Thereof We evaluated the activities of Th1 cells (T helper 1 cells) secreting the cytokine IFN-γ (Interferon-γ), Th2 cells (T helper 2 cell) secreting the cytokine IL-4 (Interleukin 4), Th17 cells (T helper 17 cell) secreting the cytokine IL-17 (Interleukin 17) and Treg cells expressing the Foxp3 transcription factor. Specifically, as shown in FIG. 5, the GVHD animal model of Example 1-2 was treated with 50 mg/kg of SD282 alone or 10 mg/kg of FK506 alone after the occurrence of GVHD. And, 10 mg/kg of FK506 and 50 mg/kg of SD282 were orally co-administrated thereto, respectively. Thereafter, the activities of the respective cells and cytokines were evaluated.

Figure 9A:
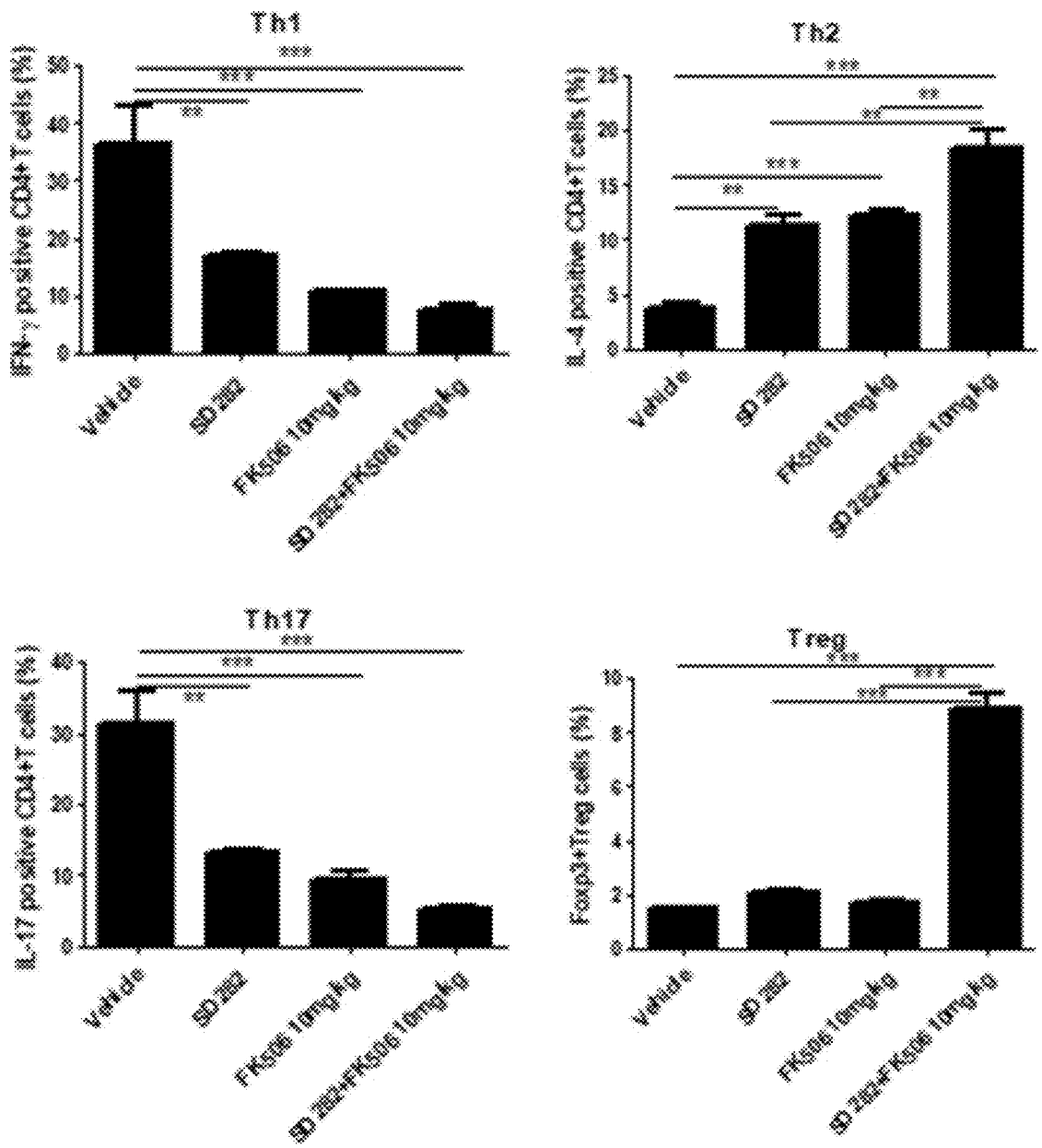
FIG. 9 is the results obtained by confirming the immune cell modulating effects by the co-treatment of SD282 and FK506 in a graft versus host disease (GVHD) animal model.

As shown in FIG. 9a, it was confirmed that the IFN-γ positive CD4+ T cells (%) and IL-17 positive CD4+ T cells (%) were significantly decreased in the group treated with the combination thereof, showing that the expressions of Th1 and Th17 cells were inhibited. And, it was confirmed that the IL-4 positive CD4+ T cells (%) and Foxp3+ Treg cells (%) were significantly increased in the group treated with the combination thereof, showing that the expressions of Th2 and Treg cells were increased.

Figure 9B:
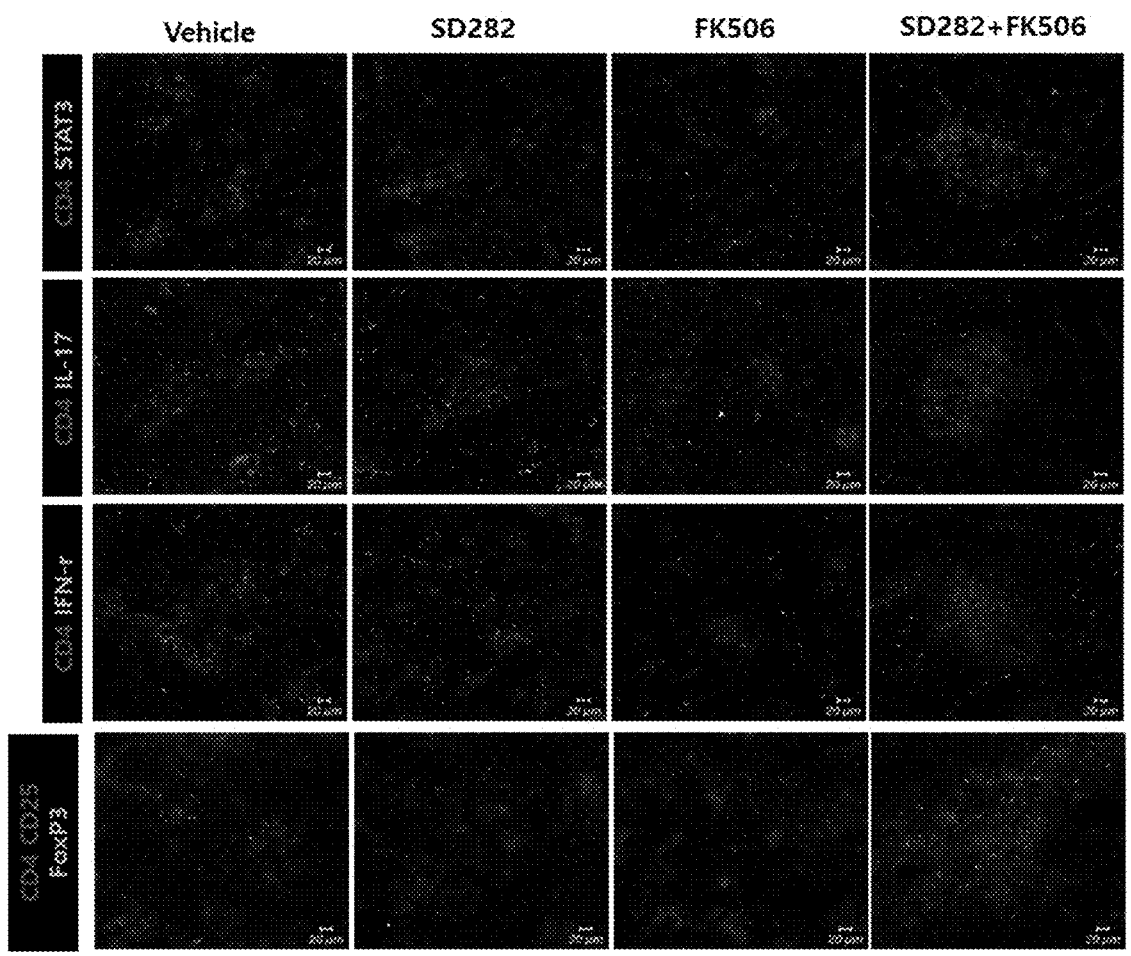
Figure 9C:
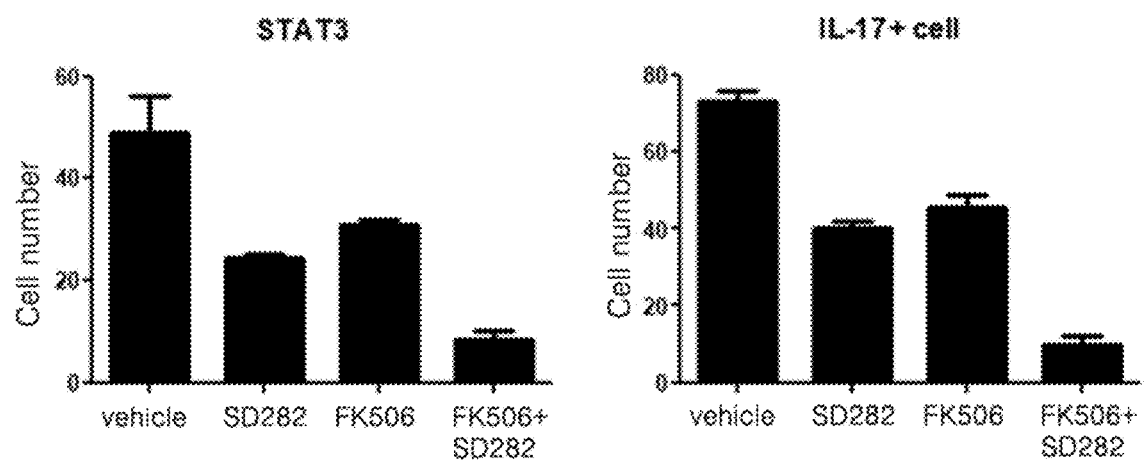
Figure 9D:
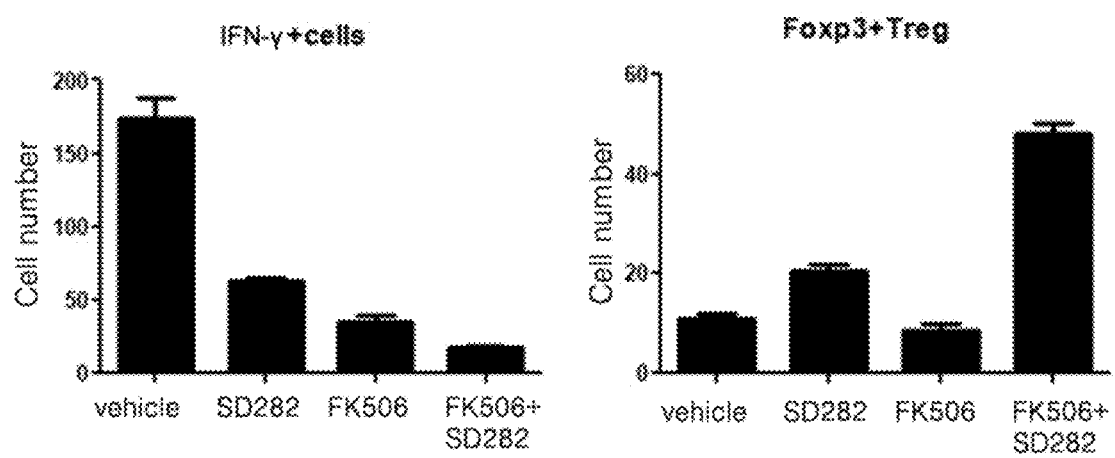

As shown in FIGS. 9b to 9d, it was confirmed that the numbers of STAT3 cell, IL-17 positive cells, and IFN-γ positive cells in the group treated with the combination thereof were decreased, showing the excellent inhibitory effects against inflammatory cytokines. In addition, it can be seen that the Foxp3+ Treg cells were remarkably increased therein.

Therefore, it was confirmed that the treatment of SD282 and FK506 in combination according to the present invention has excellent immunomodulatory ability in vivo and thus has a therapeutic effect against GVHD.

Figure 10A:
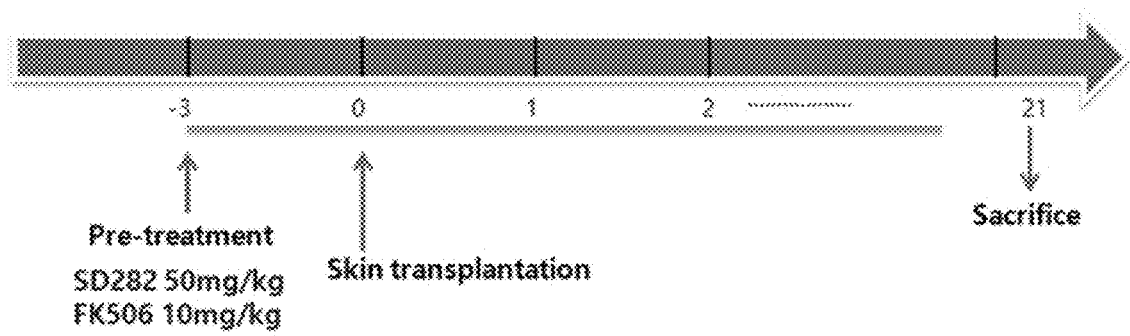
FIG. 10 is the schematic figure of an experiment for confirming effects by the co-treatment of SD282 and FK506 in a skin transplantation animal model.
Figure 10B:
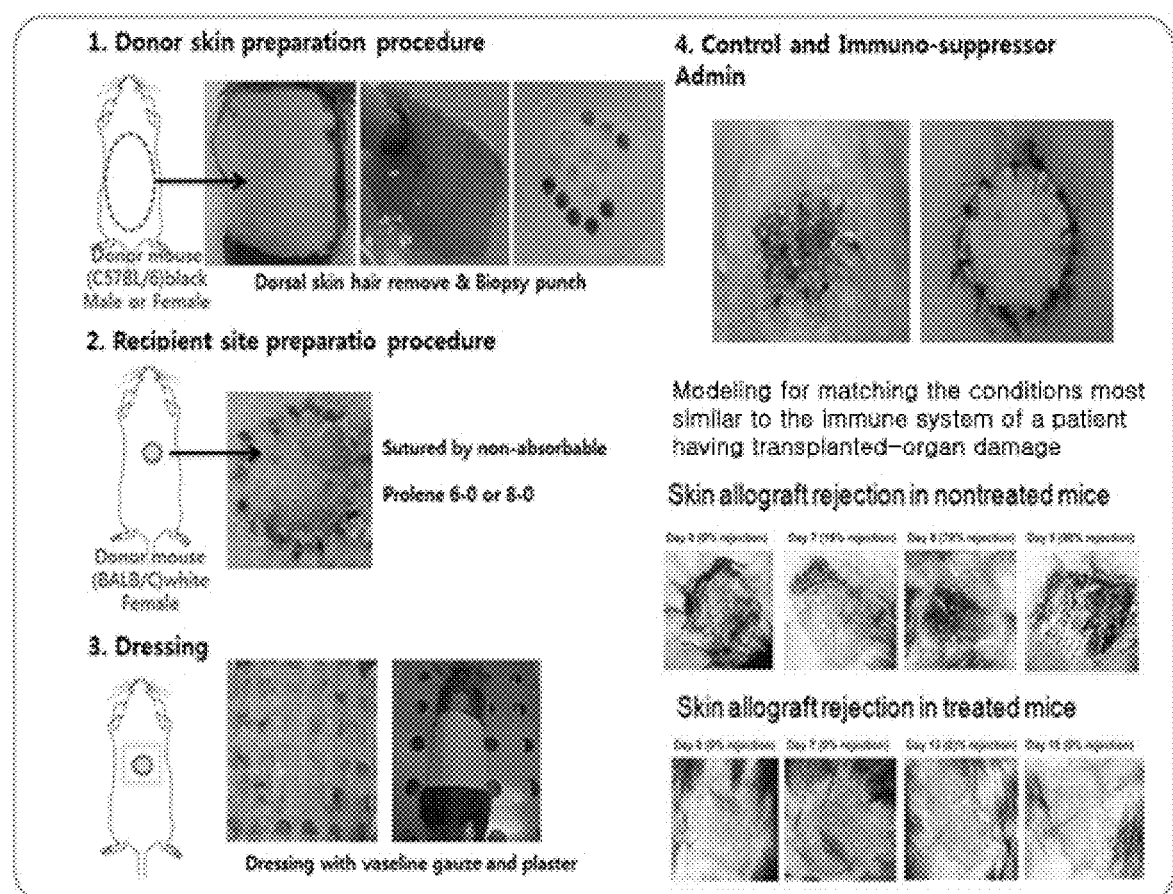

Example 5. Evaluation on Transplantation Rejections According to the Treatment of SD282 and FK506 in Combination in the Skin Transplantation Animal Model 5-1. Evaluation on Inhibitions Against Skin Transplantation Rejection According to the Treatment of SD282 Alone, FK506 Alone, or in Combination Thereof In order to evaluate the rejections after skin transplantation, the experiments were performed according to the procedures shown in FIGS. 10a and 10b, using the skin transplantation animal model of Examples 1-3. After skin transplantation, we administered 50 mg/kg of SD282 alone or 10 mg/kg of FK506 alone thereto. And, 10 mg/kg of FK506 and 50 mg/kg of SD282 were orally co-administrated thereto, respectively. Thereafter, epidermal thickness was measured to evaluate the engraftment levels of the transplanted skin tissues, followed by analyses with a H&E (haematoxylin and eosin) stain.

Figure 11:
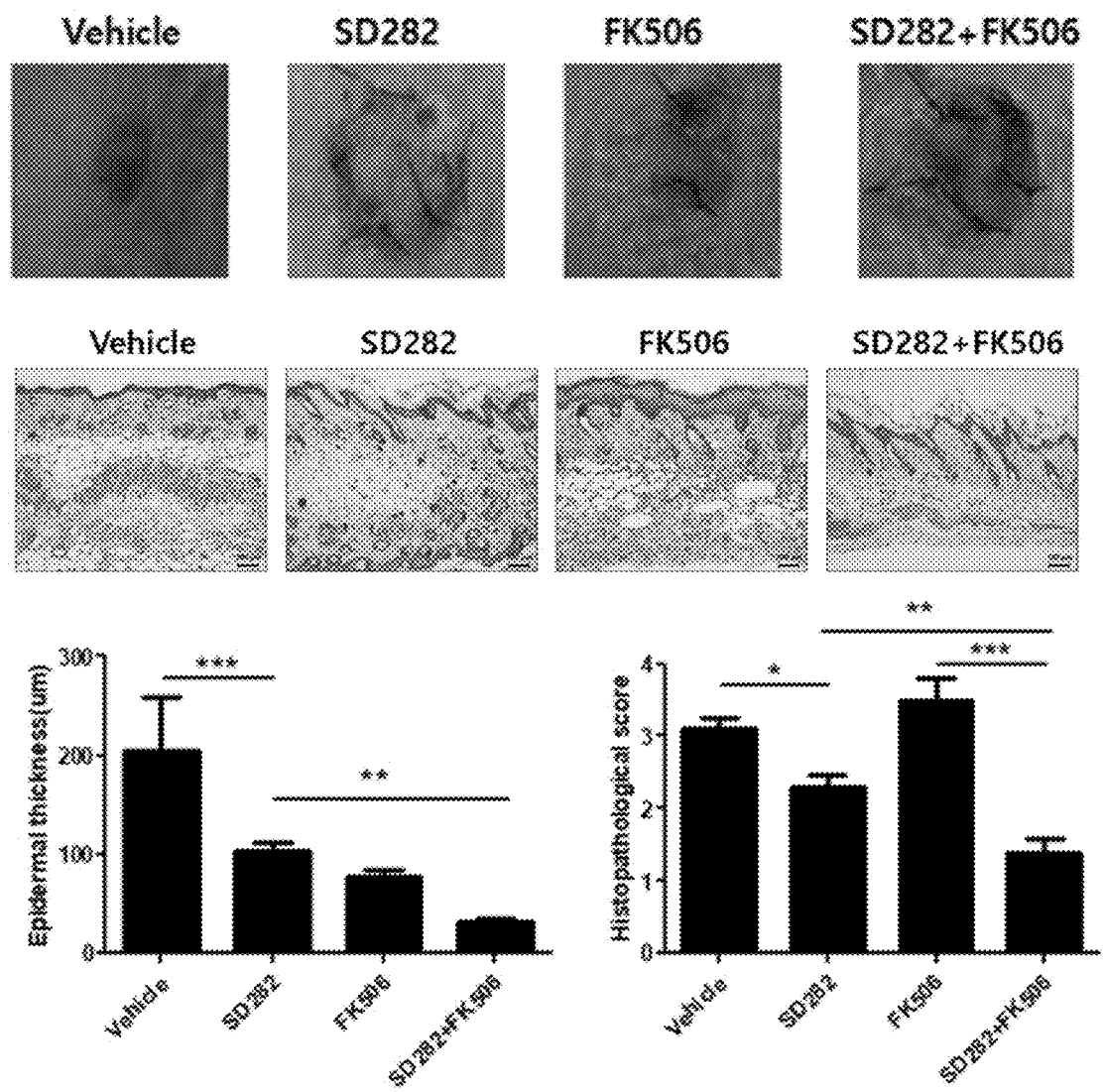
FIG. 11 is the results obtained by confirming the increasing survival rates of the grafts and the inhibitory effects against pathogenesis after skin transplantation, by the co-treatment of SD282 and FK506 in a skin transplantation animal model.

As shown in FIG. 11, it was confirmed that the epidermal thickness of the graft in the group treated with SD282 and FK506 in combination was thinner than that in the control group, showing the excellent skin tissue engraftment and the low damage to the grafted skin tissue. Accordingly, it was confirmed that the survival rate of the graft was increased and inflammatory cell infiltration was reduced, thereby inhibiting the pathogenesis.

5-2. Evaluation on the Abilities for Modulating Immune Activity According to the Treatment with SD282 Alone, FK506 Alone, or in Combination Thereof In order to evaluate the cytokine IL-17 secretion of Th17 cells, the activity of Treg cells expressing the Foxp3 transcription factor, and the ability to regulate STAT3, we obtained the transplanted sites at 21 days after the skin transplantation in the skin animal model according to the same conditions as in the above Example, and then evaluated the activity levels of STAT3, phosphorylated STAT3 (pSTAT3(Tyr705) and pSTAT3 (Ser727)), IL-17 and Foxp3 in the tissues.

Figure 12A:
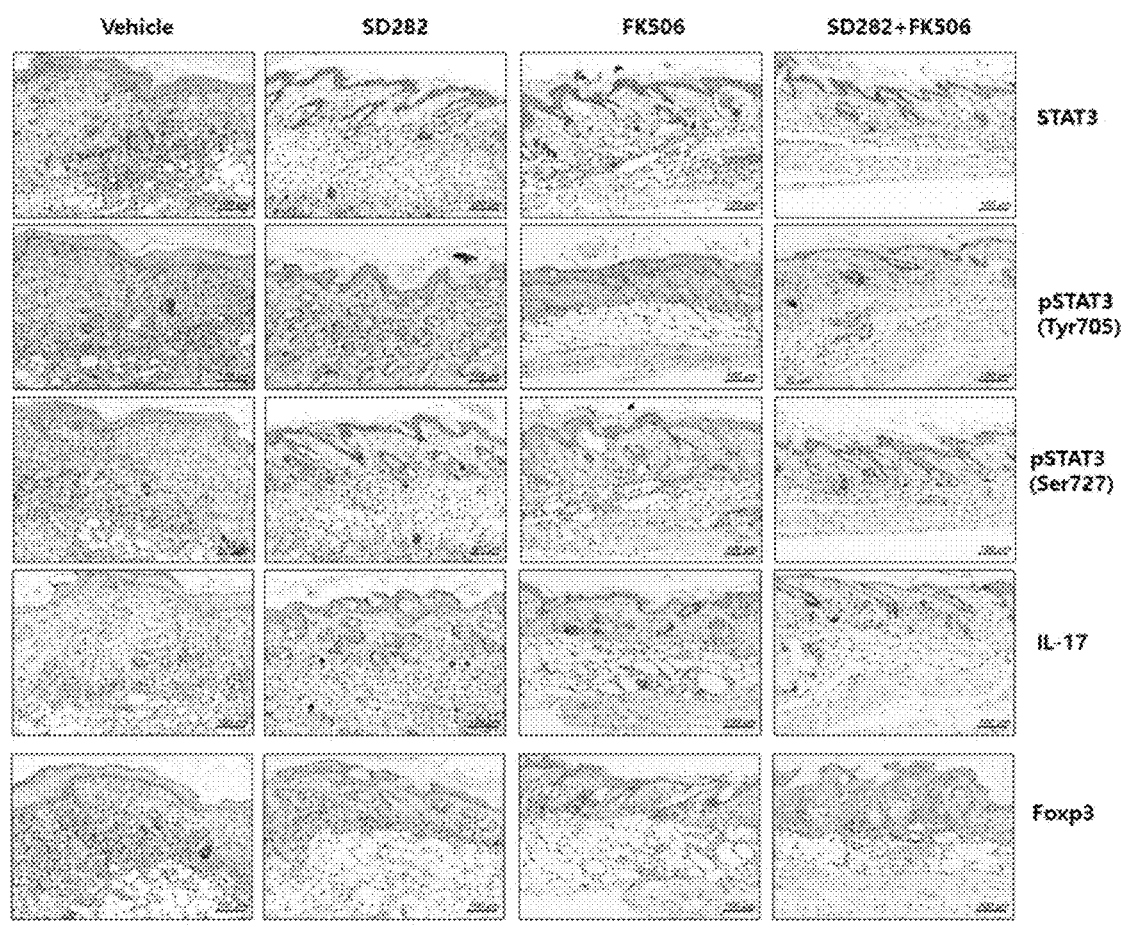
FIG. 12 is the results obtained by confirming the changes in biomarkers after skin transplantation, by the co-treatment of SD282 and FK506 in a skin transplantation animal model.
Figure 12B:
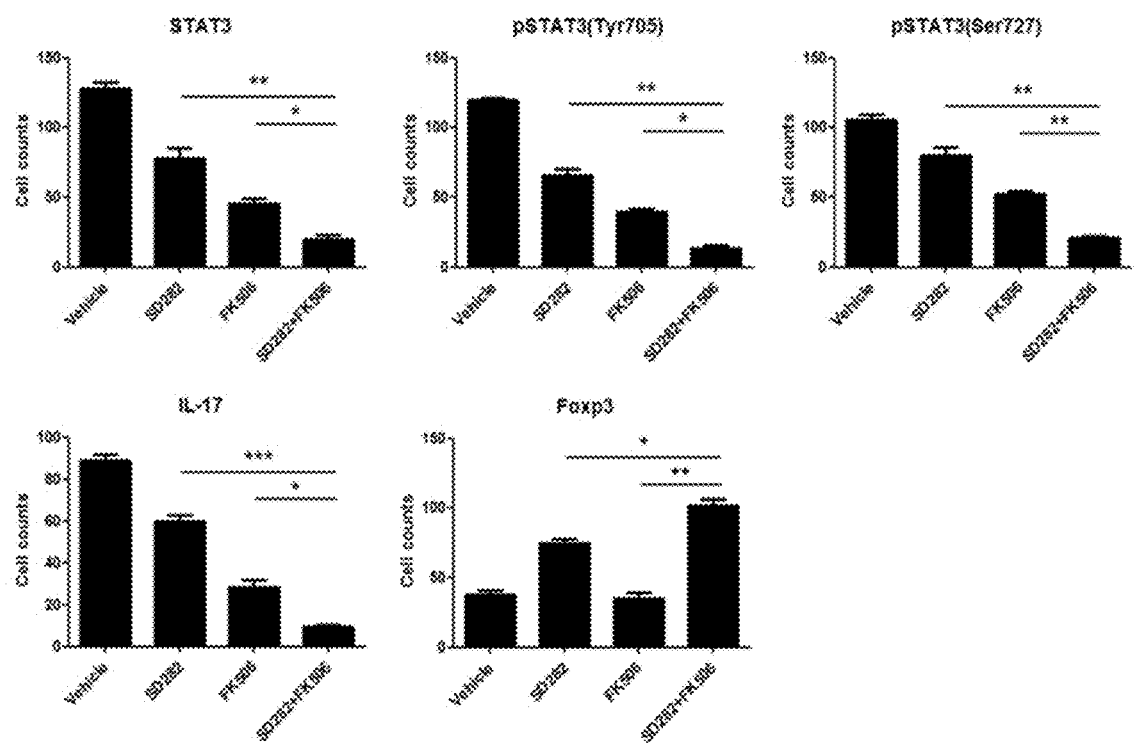

As shown in FIGS. 12a and 12b, it was confirmed that the expressions of STAT3, phosphorylated STAT3 (pSTAT3 (Tyr705) and pSTAT3 (Ser727)), and IL-17 in the group treated with SD282 and FK506 in combination were significantly decreased, in comparison with those of the group administered with SD282 alone or FK506 alone. In addition, it was confirmed that the Foxp3 expression was increased, suggesting that the treatment of SD282 and FK506 in combination has an excellent ability for modulating immune activity.

Therefore, it was confirmed that the treatment of SD282 and FK506 in combination according to the present invention inhibited the transplantation rejection of the transplanted animal model in vivo.

Example 6. Evaluation on T Cell Proliferations According to the Treatment with SD282 Alone, FK506 Alone, or in Combination Thereof in Normal Human Cells In order to evaluate the T cell proliferations according to the treatment with SD282 alone, FK506 alone, or in combination thereof in normal human PBMCs (peripheral blood mononuclear cells, PBMCs), mixed leukocyte reaction (MLR) and CFSE (carboxyfluorescein succinimidyl ester) staining were performed. An untreated syngenic group and an untreated allogenic group were used as controls. The allogenic model was treated with 50, 250 and 500 μM of SD282 alone or 1 and 5 nM of FK506 alone. And, FK506 (1 and 5 nM) and SD282 (250 μM) were treated in combination, respectively. After the treatments, each group was cultured for 4 days and then alloresponses were evaluated by observing the T cell proliferations of the cultured cells, according to the 3H-thymidine incorporation method or the flow cytometry method.

Figure 13A:
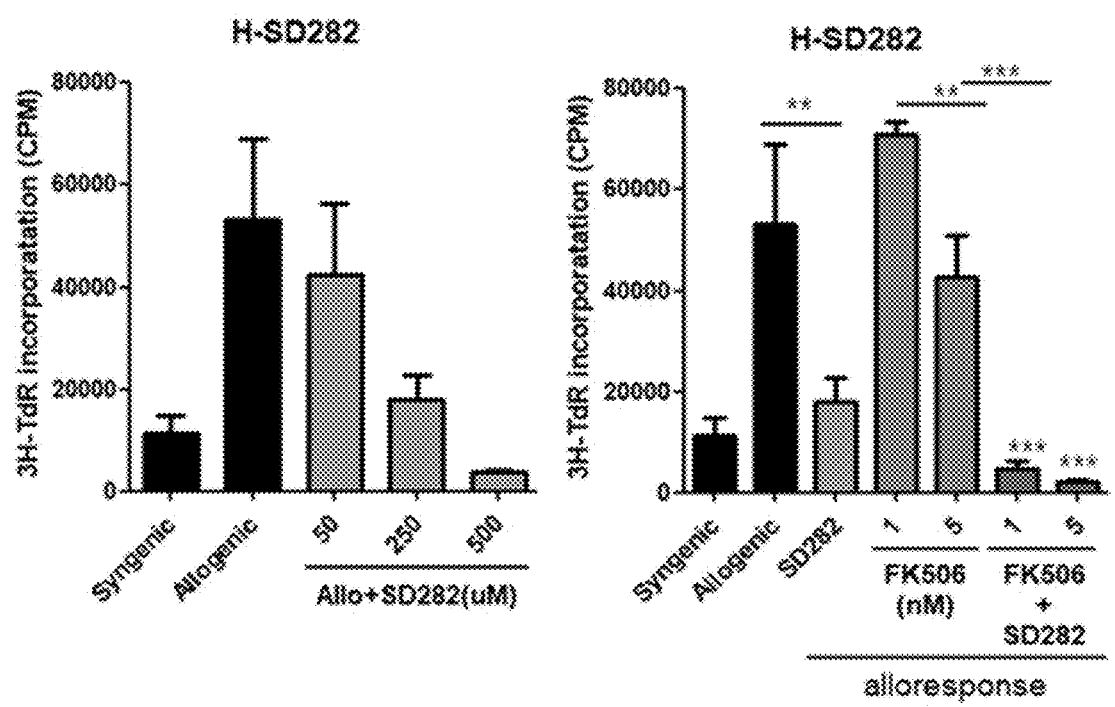
FIG. 13 is the results obtained by confirming the immunomodulatory effects by the co-treatment of SD282 and FK506 under the human allo-response conditions.
Figure 13B:
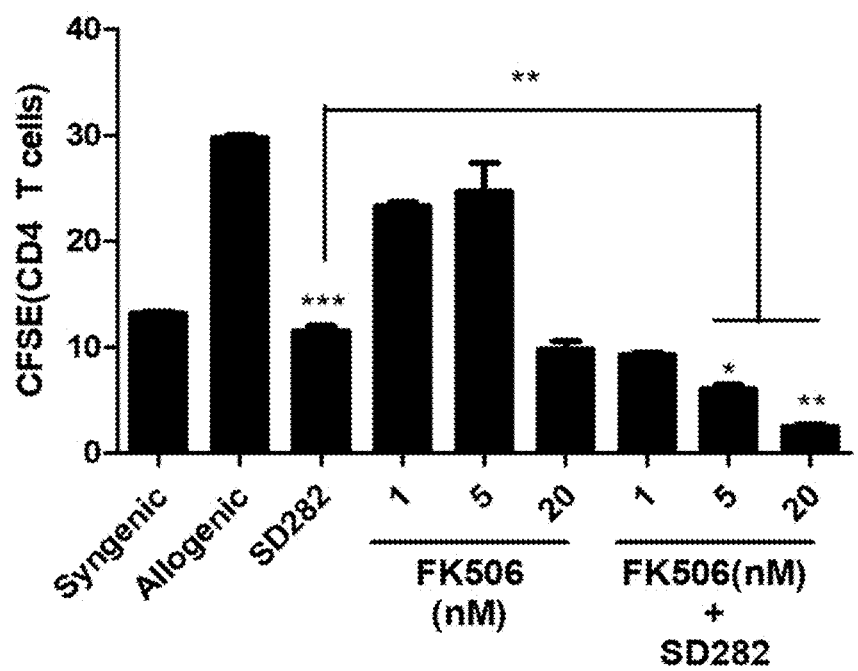

As shown in FIG. 13a, the T cell proliferation was not inhibited in the untreated allogenic group, but it was confirmed that the T cell proliferation was inhibited when 50 nM or more of SD282 was treated alone, compared to the control group. In addition, as shown in FIG. 13b, it was confirmed that the inhibition in the group treated with FK506 alone was not effective, which is similar to that of the untreated group. However, it was confirmed that the treatment of SD282 alone and the treatment of SD282 and FK506 in combination significantly inhibited the proliferation of allogenic T cells.

Example 7. Evaluation on Inhibitions Against the Activities of Inflammatory Cytokines According to the Treatment with SD282 Alone, FK506 Alone, or in Combination Thereof in Normal Human Blood Cells In order to evaluate the inhibitions against the activities of inflammatory cytokines according to the treatment with SD282 alone, FK506 alone, or in combination thereof in normal human peripheral blood cells (PBMCs), an untreated syngenic group and an untreated allogenic group were used as controls. Allogenic models were treated with 5, 250 and 500 μM of SD282 alone or 1 and 5 nM of FK506 alone. And, 1 and 5 nM of FK506 and 250 μM SD282 were treated in combination, respectively. After the treatments, each group was cultured for 4 days and then the inhibitory effects against IL-17, IFN-γ and TNF-α in the cultured cells was evaluated according to the ELISA method, so as to evaluate alloresponses.

Figure 14:
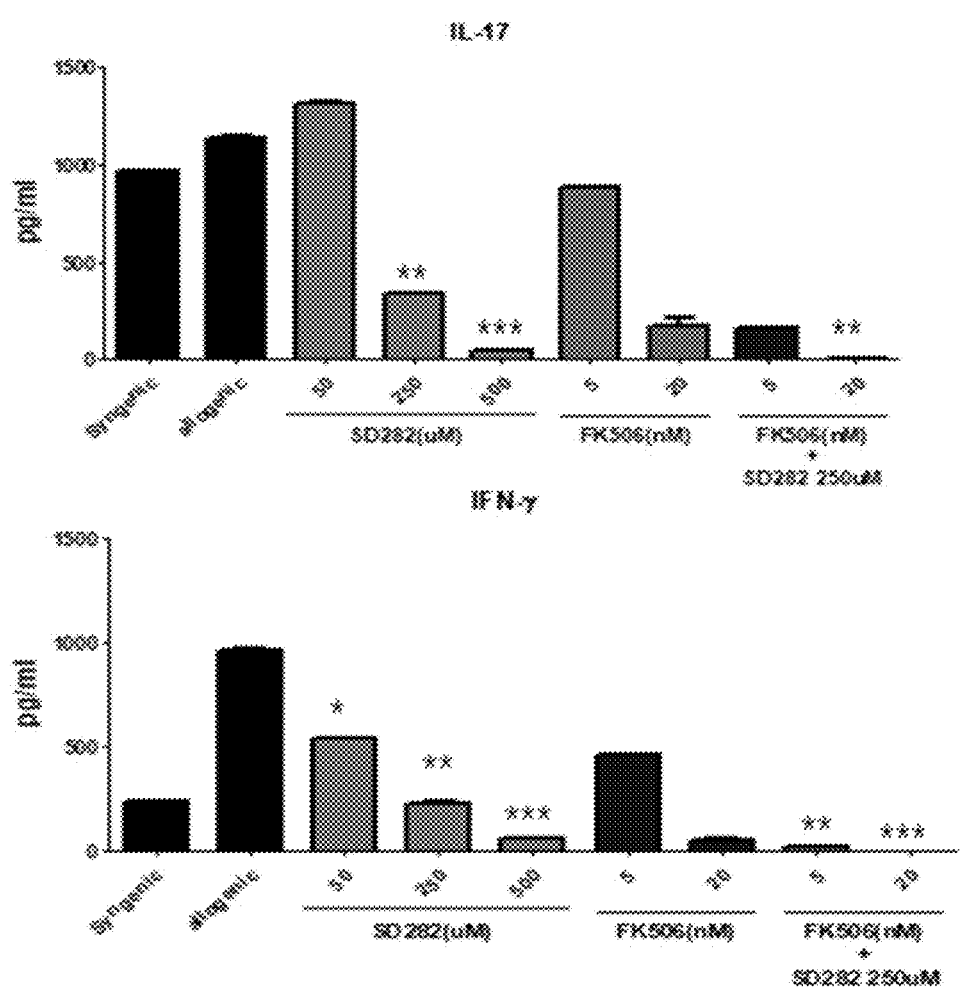
FIG. 14 is the results obtained by confirming the immunomodulatory effects by the co-treatment of SD282 and FK506 under the human allo-response conditions.
Figure 15:
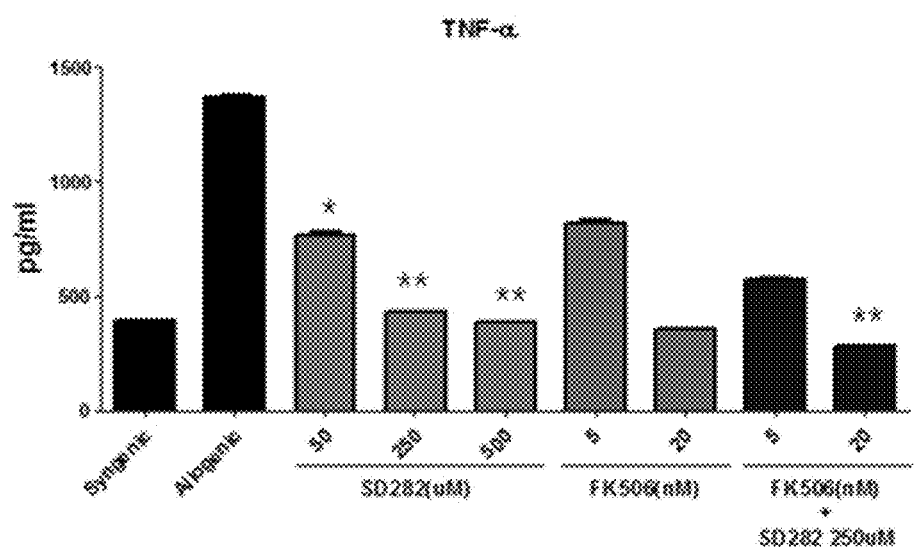
FIG. 15 is the results obtained by confirming the immunomodulatory effects by the co-treatment of SD282 and FK506 under the human allo-response conditions.

As shown in FIGS. 14 and 15, it was confirmed that the activities of IL-17, IFN-γ, and TNF-α were more significantly inhibited in the group treated with SD282 alone and the group treated with SD282 and FK506 in combination, compared to the group treated with FK506 alone.

Example 8. Evaluation on the Effects According to the Co-Administration in Liver-Transplanted Patients 8-1 Evaluation on Changes in Immune Cell Markers According to the Co-Administration Peripheral blood cells (PBMCs) were isolated from the blood of a liver-transplanted patient, using ficoll. The PBMCs were treated with 250 μM of SD282 alone, 5 nM of FK506 alone, and the combination thereof, under the condition of TCR stimulation (under the CD3 stimulation). After culturing for 4 days, immune cell subtypes were analyzed by flow cytometry to evaluate whether the Treg cell activity was induced by the respective drug treatments.

Figure 16A:
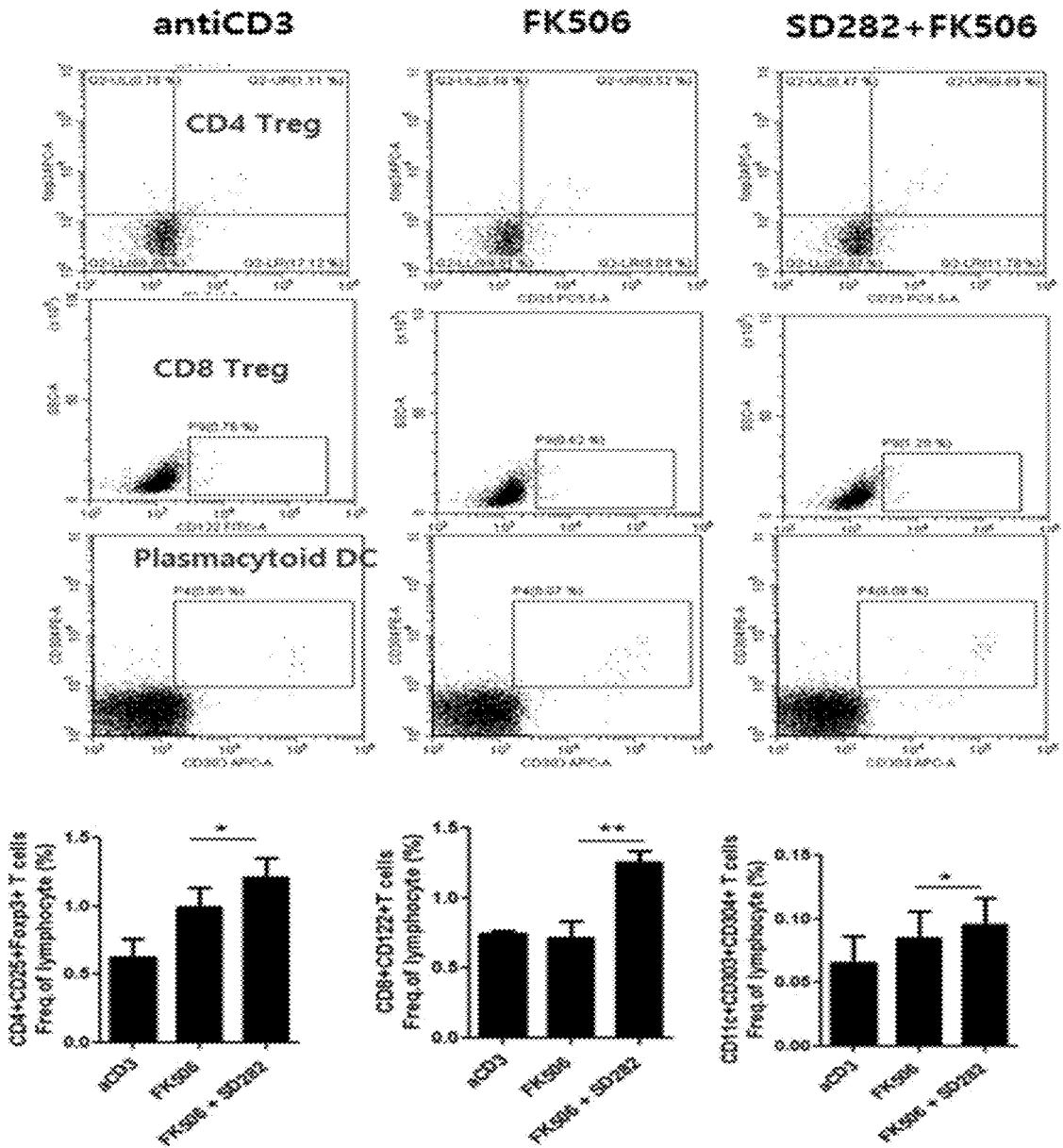
FIG. 16 is the results obtained by confirming the expression changes in immune cell markers by the co-treatment of SD282 and FK506 in the immune cells of a liver-transplanted patient.
Figure 16B:
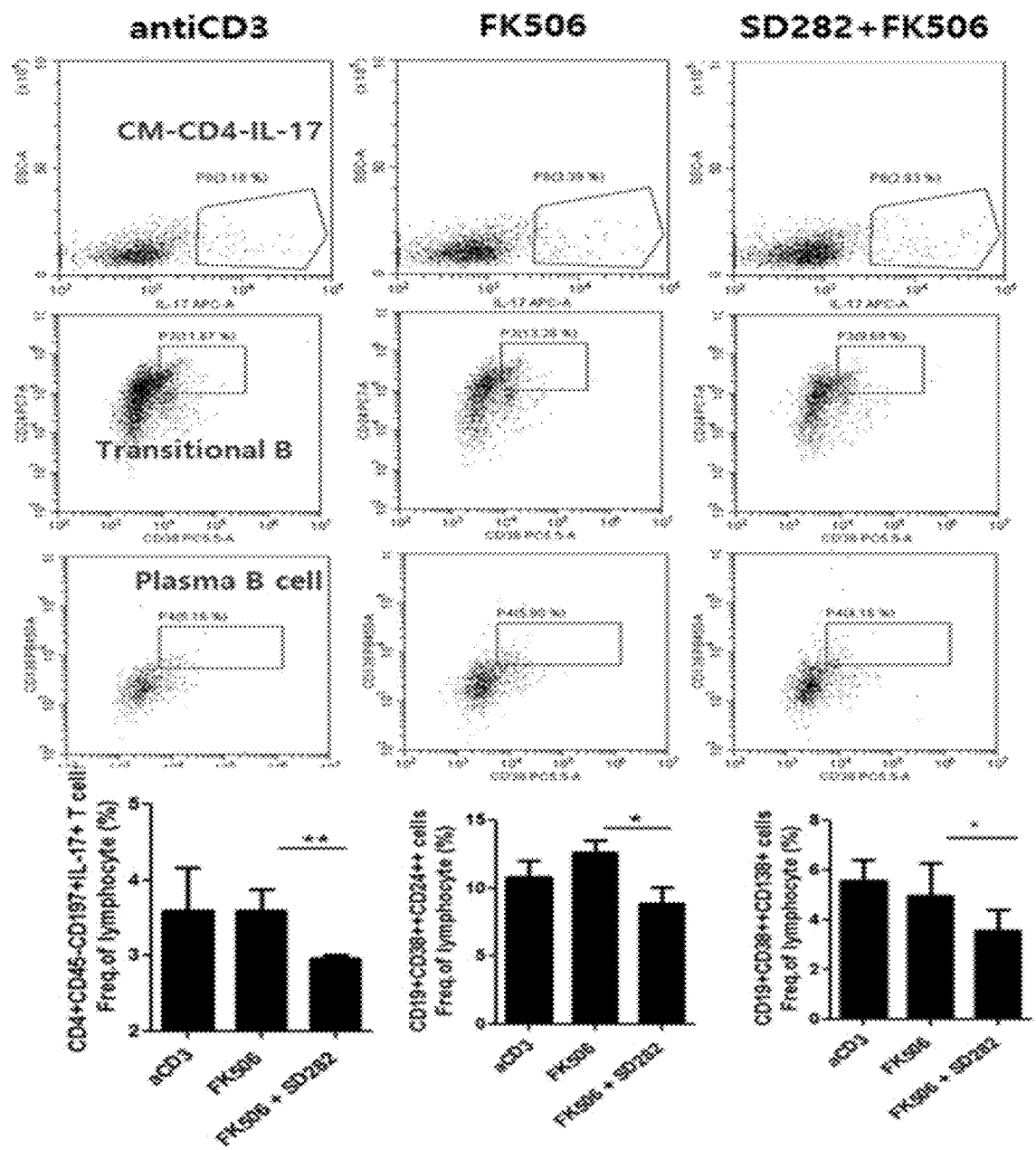

As shown in FIGS. 16a and 16b, the group treated with SD282 and FK506 in combination exhibits the increases of the immunoregulatory subtype cells (CD4+ Treg cells, CD8+ Treg cells, plasmacytoid dendritic cells); and the decreases of the transplantation rejection-related immune cell subtypes (central memory Th17 cells, transient B cells, plasma B cells).

8-2. Analyses of the KEGG Pathway and Gene Regulation According to Co-Administration In order to investigate changes in the signal factors related to immune cell modulation according to drug treatments in the peripheral blood cells (PBMCs) of a liver-transplanted patient, the PBMCs were treated with 250 μM of SD282 alone, 5 nM of FK506 alone, and the combination thereof, under the condition of TCR stimulation (under the CD3 stimulation). After culturing for 48 hours, the microarray analyses thereof were carried out by Macrogen, Inc.

Figure 17:
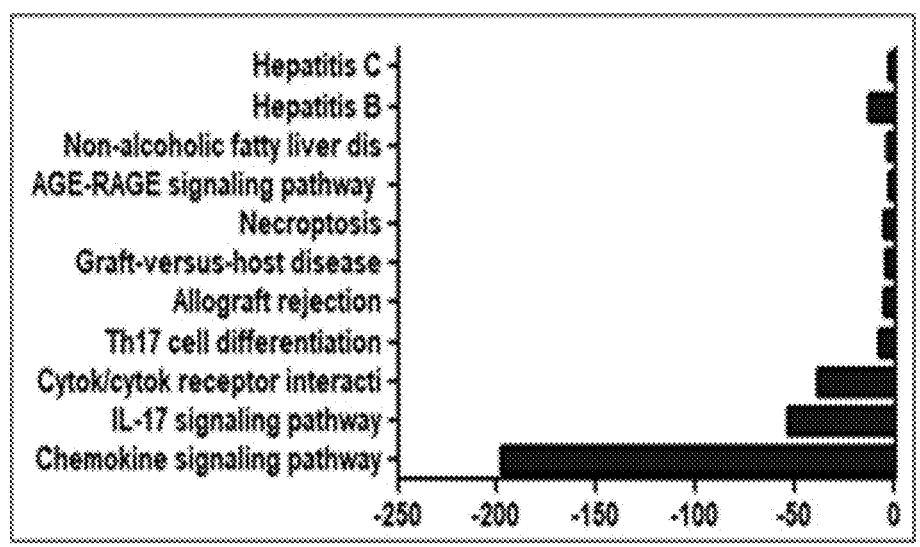
FIG. 17 is the KEGG pathways inhibited by the co-treatment of SD282 and FK506 in the liver-transplanted patients.

As shown in FIG. 17, it was confirmed that the various pathways increased in a liver-transplanted patient were inhibited by the treatment of SD282. In addition, it was confirmed that pathogenesis-related signals such as the chemokine signaling pathway and the IL-17 signaling pathway were significantly decreased by the combination of SD282 and FK506.

Figure 18A:
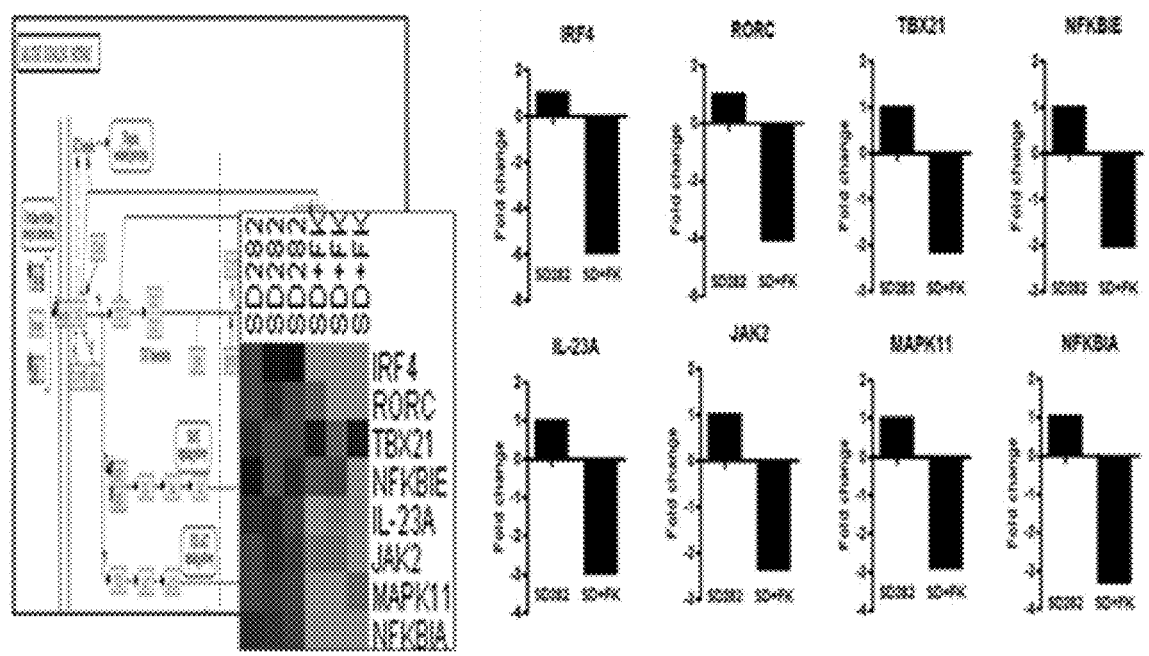
FIG. 18 is the results obtained by confirming the modulations of pathogenic cells and the gene regulatory effects, by the co-treatment of SD282 and FK506, in a liver-transplanted patient (FIG. 18a: STAT-modulating effects, FIG. 18b: mitochondrial function-recovery effect, FIG. 18c: modulating effects against cell death of inflammatory cells.
FIG. 18d: modulating effects against cell migration).
Figure 18B:
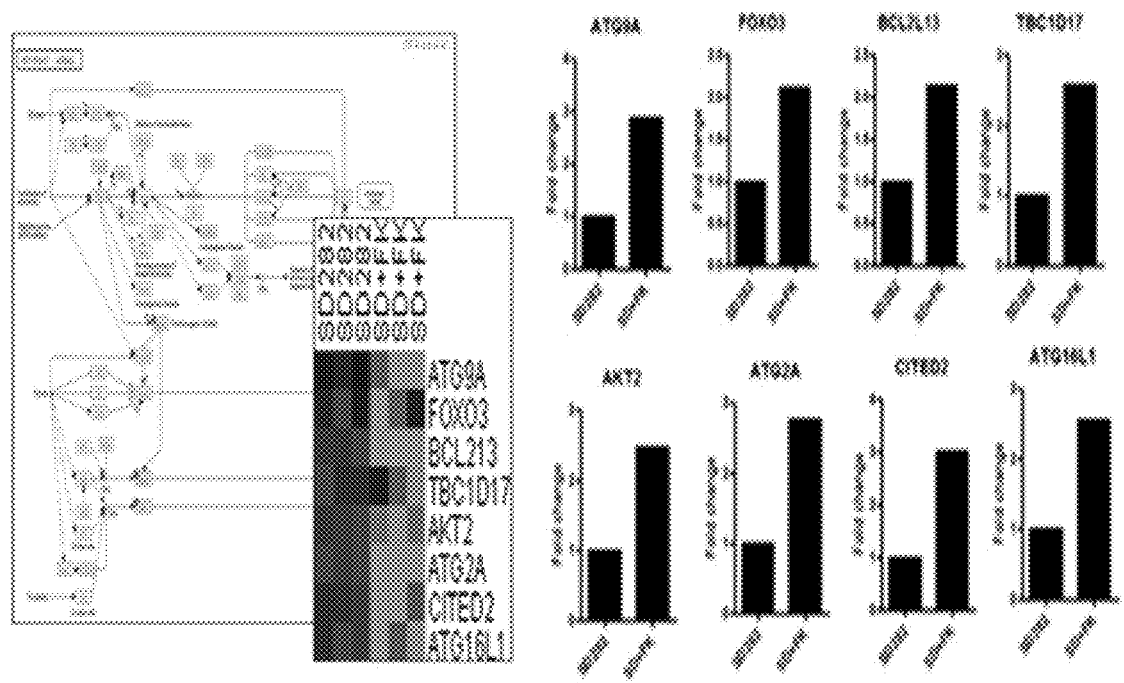
Figure 18C:
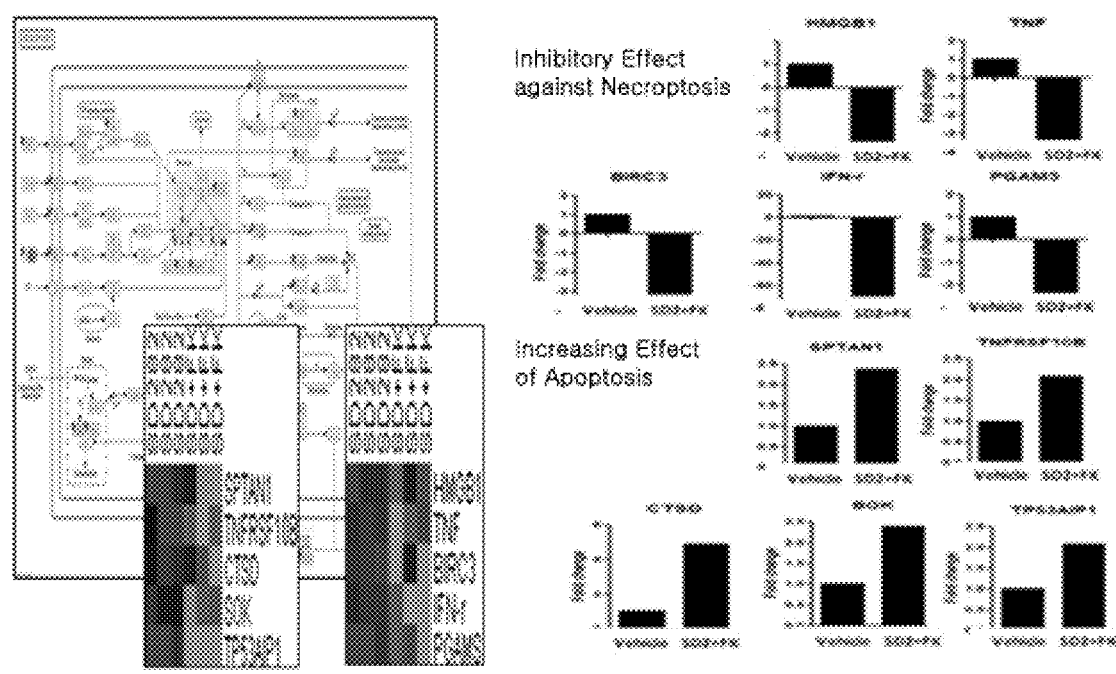
Figure 18D:
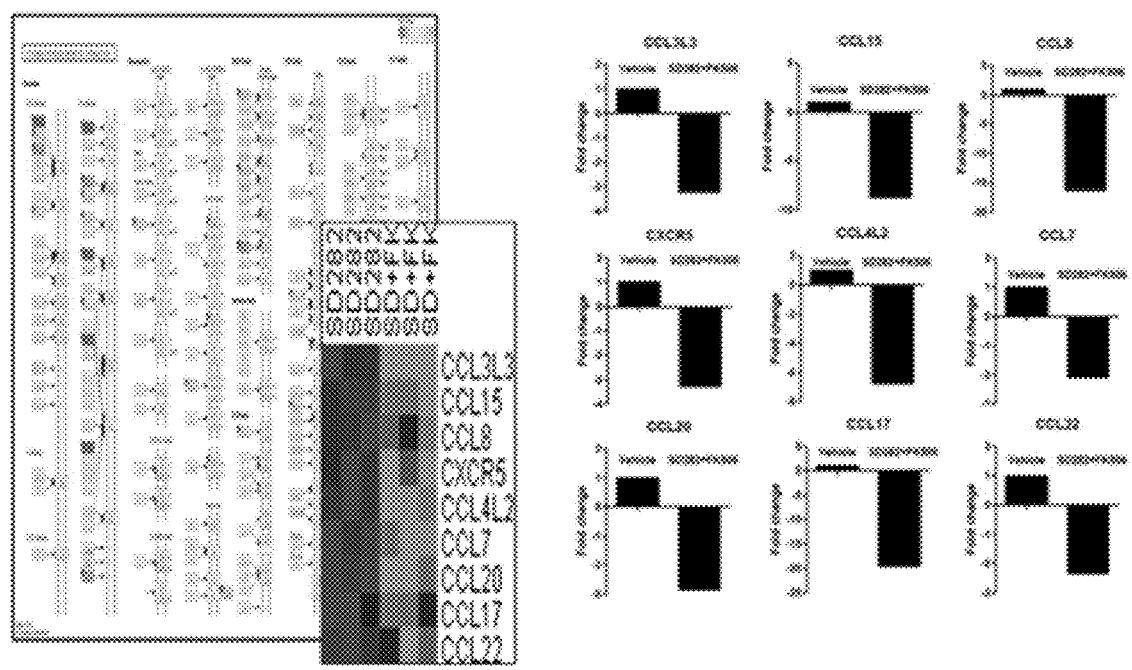

As a result of performing the analyses on what kind of genes actually increased or decreased under the above conditions, it was confirmed in FIG. 18a that the co-administration exhibited more excellent inhibitory effects against the STAT3 pathways, in comparison with the administration of SD282 alone. As shown in FIG. 18b, it was confirmed that the co-administration exhibited more excellent recovery effects of the mitochondrial function, in comparison with the administration of SD282 alone. As shown in FIG. 18c, it was confirmed that the co-administration exhibited more excellent inhibitory effects against cell death of inflammatory cells, in comparison with the administration of SD282 alone. And, as shown in FIG. 18d, it was confirmed that the co-administration exhibited more excellent inhibitory effects against cell migration, in comparison with the administration of SD282 alone.

Figure 19:
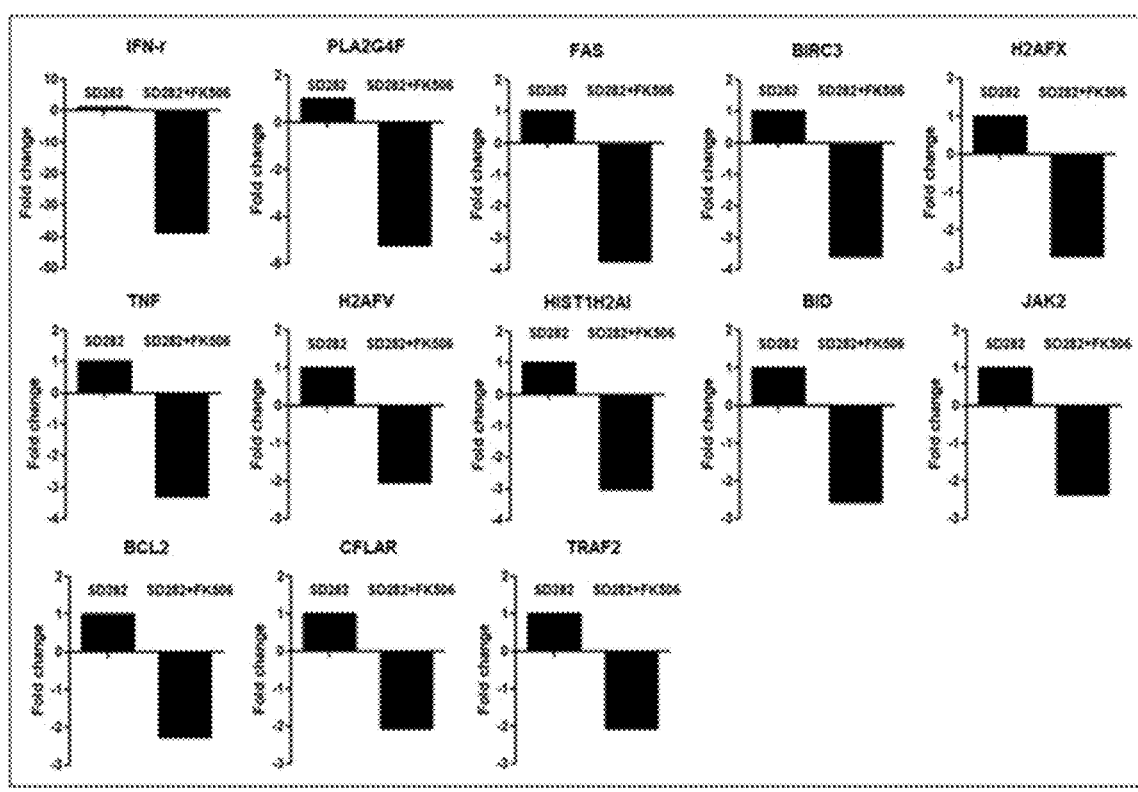
FIG. 19 is the results obtained by confirming the inhibitory effects against cell death, by the co-treatment of SD282 and FK506, in a liver-transplanted patient.

In addition, as shown in FIG. 19, it was confirmed that the co-administration exhibited more excellent inhibitory effects against cell death of immune cells, in comparison with the administration of SD282 alone.

8-3. Evaluation on Modulating Effects of Pathogenic Cell Migration in a Liver-Transplanted Patient Immune cells of a mouse and a liver-transplanted patient were treated with each drug for 48 hours, and then cells were harvested for performing the migration assay thereof. $2 \times 10^5$ cells were loaded onto the upper transwell and then incubated for 2 hours, with no treatment or with the treatment of sDF-1 in the lower chamber. After 2 hours, the number of the migrated cells was counted.

Figure 20A:
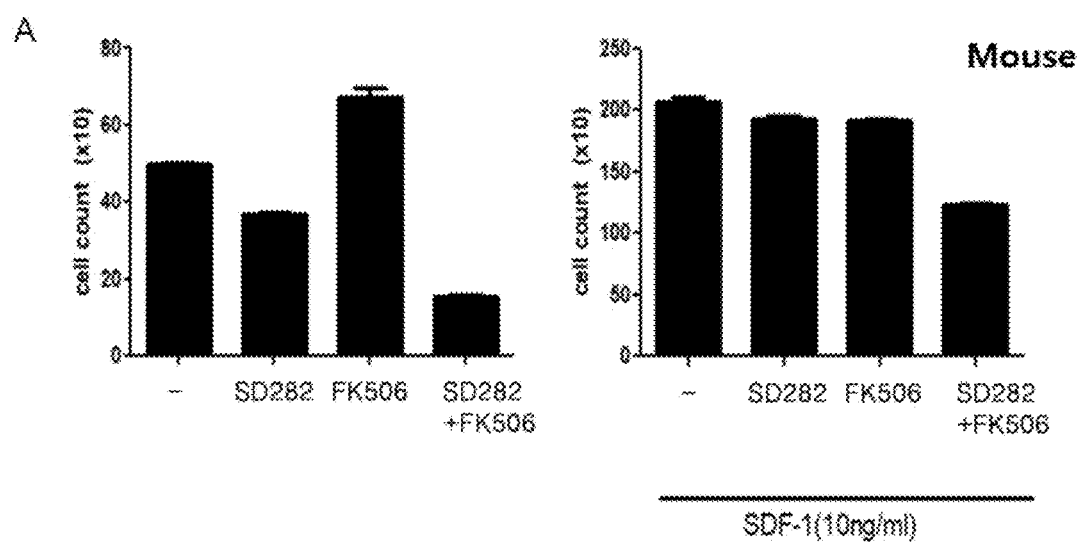
FIG. 20 is the results obtained by confirming the inhibitory effects against cell migration, by the co-treatment of SD282 and FK506, in a liver transplantation model (FIG. 20a: mouse.
FIG. 20b: human).
Figure 20B:
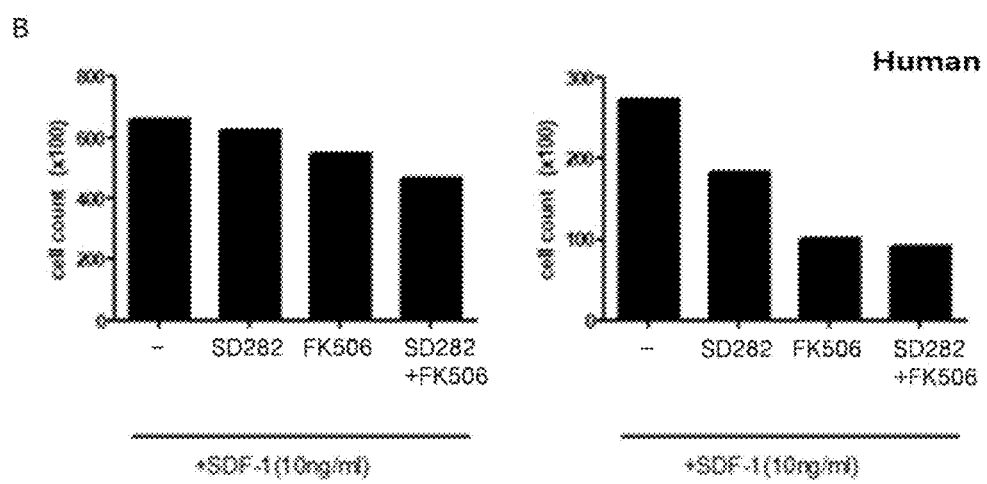

As shown in FIGS. 20a and 20b, it was confirmed that the co-treatment group exhibited more excellent inhibitory effects against cell migration, in comparison with the group treated with SD282 alone.

Example 9. Evaluation on the Efficacies in an Avatar Model of Liver-Transplanted Patients 9-1. Preparation of a Humanized Mouse Model Having Liver Injury To establish a humanized mouse model (avatar model) having liver injury, which is equipped with a human immune system, human-derived PBMCs (peripheral blood mononuclear cells) were intravenously injected into NSG mice and then liver stellate cell line was intravenously injected thereto. $CCl_4$ was injected thereto to induce liver damage (liver fibrosis). Specifically, the PBMCs derived from a normal subject or the PBMCs derived from a patient having liver disease (HBV-induced liver cirrhosis patients or alcoholic cirrhosis patients) were intravenously injected into NSG mice. After 1 day, the liver stellate cell line and $CCl_4$ were intravenously injected thereto. The engraftment of human cells was confirmed 20 days later and then the mice were sacrificed to perform tissue analyses 39 days later.

9-2. Evaluation on Inflammation or Fibrosis in the Mouse Model Having Liver Injury In the liver damage model induced by $CCl_4$ injection along with injection of the bloods derived from a normal subject or a liver-transplanted patient (prepared in 9-1), inflammation and fibrosis are more induced by the blood derived from the transplanted patients compared to the normal subjects. The levels of inflammation and fibrosis were evaluated according to the treatment alone or treatments in combination.

Figure 21A:
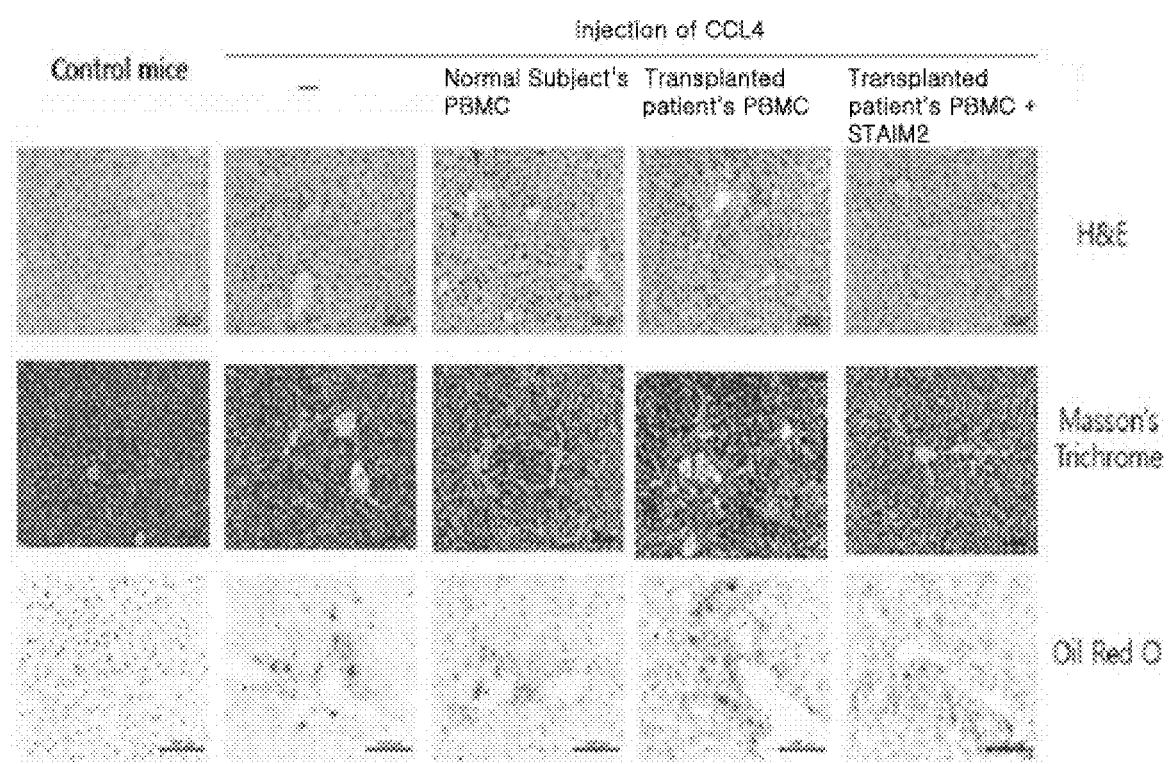
FIG. 21 is the results obtained by confirming the levels of inflammation and fibrosis in the avatar model of a liver-transplanted patient.
Figure 21B:
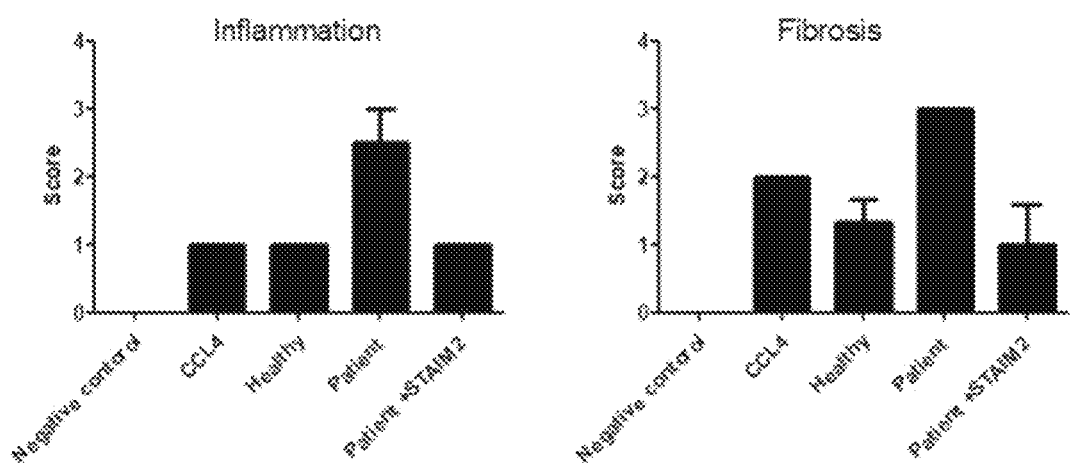

As shown in FIGS. 21a and 21b, it was confirmed that the treatment of the combination exhibited significantly decreased inflammation and fibrosis, in comparison with the treatment of SD282 alone.

The invention claimed is:

1. A pharmaceutical composition for preventing or treating transplantation rejection or a transplantation rejection disease, comprising 1) a compound represented by the following formula 1 or a pharmaceutically acceptable salt thereof and 2) a calcineurin inhibitor or a pharmaceutically acceptable salt thereof as active ingredients:

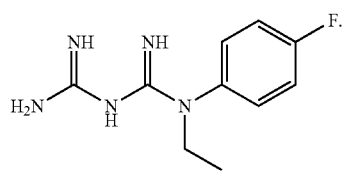
<Formula 1>

2. The pharmaceutical composition of claim 1, wherein the calcineurin inhibitor is FK506 (tacrolimus) or cyclosporine.

3. The pharmaceutical composition of claim 1, wherein the transplantation rejection is one or more transplantation rejections selected from the group consisting of cells, blood, tissues and organs.

4. The pharmaceutical composition of claim 3, wherein the transplantation rejection is one or more selected from the group consisting of bone marrow transplantation rejection, heart transplantation rejection, corneal transplantation rejection, bowel transplantation rejection, liver transplantation rejection, lung transplantation rejection, pancreas transplantation rejection, kidney transplantation rejection, and skin transplant rejection.

5. The pharmaceutical composition of claim 1, wherein the transplantation rejection disease is graft-versus-host disease (GVHD).

6. The pharmaceutical composition of claim 1, wherein the composition inhibits a proliferation of T cells.

7. The pharmaceutical composition of claim 1, wherein the composition decreases a differentiation of undifferentiated T cells to Th1 cells or Th17 cells; or an activity of Th1 cells or Th17 cells.

8. The pharmaceutical composition of claim 1, wherein the composition increases a differentiation of undifferentiated T cells to Treg cells and an activity of Treg cells.

9. A pharmaceutical composition for immunosuppression after transplantation, comprising 1) a compound represented by the following formula 1 or a pharmaceutically acceptable salt thereof and 2) a calcineurin inhibitor or a pharmaceutically acceptable salt thereof as active ingredients:

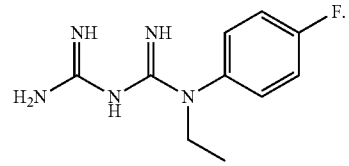
<Formula 1>

10. A method for treating transplantation rejection or a transplant rejection disease, comprising administering 1) a compound represented by the following formula 1 or a pharmaceutically acceptable salt thereof and 2) a calcineurin inhibitor or a pharmaceutically acceptable salt thereof to a subject in need thereof:

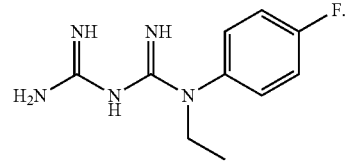
<Formula 1>

11. A method for immunosuppression after transplantation, comprising administering 1) a compound represented by the following formula 1 or a pharmaceutically acceptable salt thereof and 2) a calcineurin inhibitor or a pharmaceutically acceptable salt thereof to a subject in need thereof:

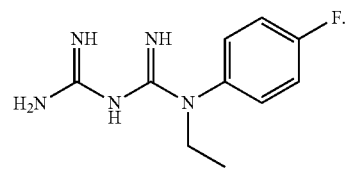
<Formula 1>

* * * * *